US007659053B2

(12) United States Patent
Jiang et al.

(10) Patent No.: US 7,659,053 B2
(45) Date of Patent: Feb. 9, 2010

(54) METHODS OF ALTERATION OF SURFACE AFFINITIES USING NON-CHEMICAL FORCE-CREATING FIELDS

(75) Inventors: Xingyu Jiang, Cambridge, MA (US); Rosaria Ferrigno, Grenoble (FR); George M. Whitesides, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/181,371

(22) Filed: Jul. 14, 2005

(65) Prior Publication Data

US 2006/0063276 A1    Mar. 23, 2006

Related U.S. Application Data

(63) Continuation of application No. PCT/US2004/002498, filed on Jan. 29, 2004.

(60) Provisional application No. 60/443,466, filed on Jan. 29, 2003.

(51) Int. Cl.
     *C12Q 1/00*      (2006.01)
     *G01N 33/53*      (2006.01)

(52) U.S. Cl. .......................... 435/4; 435/7.1; 436/514; 436/53; 436/823

(58) Field of Classification Search .................. 435/4, 435/7.2, 7.1, 287.2; 436/528, 524, 53, 80, 436/823; 530/404, 408; 568/21
See application file for complete search history.

(56) References Cited

U.S. PATENT DOCUMENTS

| | | | |
|---|---|---|---|
| 5,079,600 | A | 1/1992 | Schnur et al. |
| 5,143,854 | A | 9/1992 | Pirrung et al. |
| 5,143,857 | A | 9/1992 | Finchem et al. |
| 5,352,485 | A * | 10/1994 | DeGuire et al. ............. 427/226 |
| 5,512,131 | A | 4/1996 | Kumar et al. |
| 5,776,748 | A | 7/1998 | Singhvi et al. |
| 5,900,160 | A | 5/1999 | Whitesides et al. |
| 5,976,826 | A | 11/1999 | Singhvi et al. |
| 6,180,239 | B1 | 1/2001 | Whitesides et al. |
| 6,355,198 | B1 | 3/2002 | Kim et al. |
| 6,368,838 | B1 | 4/2002 | Singhvi et al. |
| 6,472,148 | B1 | 10/2002 | Bamdad et al. |
| 6,756,354 | B2 * | 6/2004 | Nelson ........................ 514/2 |
| 6,764,768 | B2 | 7/2004 | Mrksich et al. |
| 6,893,850 | B2 | 5/2005 | Ostuni et al. |
| 2002/0006626 | A1 * | 1/2002 | Kim et al. .................. 435/7.1 |
| 2002/0119305 | A1 | 8/2002 | Mrksich et al. |
| 2003/0032048 | A1 * | 2/2003 | Kim et al. ................... 435/6 |
| 2005/0253139 | A1 * | 11/2005 | Gorman et al. .............. 257/46 |
| 2006/0081479 | A1 * | 4/2006 | Mirkin et al. ............... 205/640 |

FOREIGN PATENT DOCUMENTS

| | | |
|---|---|---|
| DE | 19711661 | 12/1997 |
| GB | 369382 | 3/1932 |
| WO | WO 97/14752 | 4/1997 |
| WO | WO 01/89788 | 11/2001 |
| WO | WO 02/06407 | 1/2002 |
| WO | WO 03/076718 | 9/2003 |

OTHER PUBLICATIONS

Wilhelm et al. Patterns of functional proteins formed by local electrochemical desorption of self-assembled monolayers. Electrochemica Acta 2001, vol. 47, pp. 275-281.*

Huang et al. Electric manipulation of bioparticles and macromolecules on microfabricated electrodes. Anal. Chaem. 2001, vol. 73, pp. 1549-1559.*

Hobara, D., et al., "Surface Structure of Binary Self-Assembled Monolayers Formed by Electrochemical Selective Replacement of Adsorbed Thiols," *Langmuir*, vol. 15, pp. 5073-5078 (1999).

Jiang, X., et al., "Electrochemical Desorption of Self-Assembled Monolayers Non-Invasively Releases Patterned Cells from Geometrical Confinements," *J. Am. Chem. Soc.*, vol. 124, pp. 2366-2367 (2003).

(Continued)

*Primary Examiner*—Shafiqul Haq
(74) *Attorney, Agent, or Firm*—Wolf, Greenfield & Sacks, P.C.

(57) ABSTRACT

The present invention provides a series of methods, compositions, and articles for altering a property of a surface (for example, the cytophilicity and/or the hydrophilicity), by exposing at least a portion of the surface to a non-chemical, force-creating field and/or force, such as an electric field. The field/force may be created by any suitable technique. For instance, the field can be created by applying a voltage across the surface, by electrical induction, etc. In certain embodiments, the surface includes molecules attached thereto that can be detached when exposed to non-chemical, force-creating fields and/or forces, thereby altering the chemical composition of at least a portion of the surface. In one set of embodiments, the molecules attached to the surface may include molecules forming a self-assembled monolayer on the surface. In some embodiments, the molecules attached to the surface may include thiol moieties (e.g., as in an alkanethiol), by which the molecule can become attached to the surface. In certain cases, the molecules may be terminated at the unattached end with one or more hydrophilic groups, for example, unmodified ethylene glycol moieties. In some cases, the molecules attached to the surface may include one or more moieties that can bind to various entities such as proteins, peptides, nucleic acids, drugs, cells, etc. In certain embodiments, the techniques are used to enable novel assays for cell motility and/or spreading and screening tests for determining drugs and/or treatments effective in increasing or decreasing cell shape changes and/or motility on surfaces.

9 Claims, 11 Drawing Sheets

OTHER PUBLICATIONS

Kim, et al., Electrochemical Deposition for Site-Selective Immobilization of Biomolecules, *Langmuir*, 18:1460-1462 (2002).

Tender, L.M., et al., "Electrochemical Patterning of Self-Assembled Monolayers onto Microscopic Arrays of Gold Electrodes Fabricated by Laser Ablation," *Langmuir*, vol. 12, pp. 5515-5518 (1996).

Yang, D.F., et al., "Studies of the Electrochemical Removal and Efficieint Re-formation of a Monolayer of Hexadecanethiol Self-Assembled at an Au(111) Single Crystal in Aqueous Solution," *Langmuir*, vol. 13, pp. 243-249 (1997).

International Search Report for PCT/US2004/002498 dated Oct. 11, 2004.

Written Opinion for PCT/US2004/002498 dated Oct. 11, 2004.

Amit, B., et al., "Photosensitive Protecting Groups of Amino Sugars and Their Use in Glycoside Synthesis.2-Nitrobenzyloxycarbonylamino and 6-Nitroveratrylyloxycarbony lamino Derivatives," *J. Org. Chem.*, vol. 39, No. 2, pp. 192-196 (1974).

Ben-Ze'Ev, A., "Protein Synthesis Requires Cell-Surface Contact while Nuclear Events Respond to Cell Shape in Anchorage-Dependent Fibroblasts," *Cell*, vol. 21, pp. 365-372 (1980).

Bhatia, S., et al., "Fabrication of Surfaces Resistant to Protein Adsorption and Application to Two-Dimensional Protein Patterning," *Analytical Biochemistry*, vol. 208, pp. 197-205 (1993).

Bhatia, S., et al., "New Approach to Producing Patterned Biomolecular Assemblies," *J. Am. Chem. Soc.*, vol. 114, pp. 4432-4433 (1992).

Britland, S., et al., "Micropatterened Substratum Adhesiveness: A Model for Morphogenetic Cues Controlling Cell Behavior," *Experimental Cell Research*, vol. 198, pp. 124-129 (1992).

Brunette, D.M., "Spreading and Orientation of Epithelial Cells on Grooved Substrata," *Experimental Cell Research*, vol. 167, pp. 203-217 (1986).

Chehroudi, B., et al., "Effects of a grooved epoxy substratum on epithelial cell behavior in vitro and in vivo," *Journal of Biomedical Materials Research*, vol. 22, pp. 459-473 (1988).

Chehroudi, B., et al., "Titanium-coated micromachined grooves of different dimensions affect epithelial and connective-tissue cells differently in vivo," *Journal of Biomedical Materials Research*, vol. 24, pp. 1203-1219 (1990).

Clark, P., et al., "Topographical control of cell behavior," *Development*, vol. 99, pp. 439-448 (1987).

Dunn, G.A., et al., "Alignment of Fibroblasts on Grooved Surfaces described by a simple geometric transformation," *J. Cell Sci.*, vol. 83, pp. 313-340 (1986).

Folkman, J., et al., "Role of cell shape in growth control.," *Nature*, vol. 273, pp. 345-349 (1978).

Gospodarowicz, D., et al., "Determination of Cellular Shape by the Extracellular Matrix and Its Correlation with the Control of Cellular Growth," *Cancer Research*, vol. 38, pp. 4155-4171 (1978).

Ingber, D.E., et al., "Endothelial Growth Factors and Extracellular Matrix Regulate DNA Synthesis through Modulation of Cell and Nuclear Expansion," In Vitro *Cellular & Developmental Biology*, vol. 23, No. 5, pp. 387-394 (1987).

Ingber, D.E., et al., "Mechanochemical Switching between Growth and Differentiation during Fibroblast Growth Factor-stimulated Angiogenesis In Vitro: Role of Extracellular Matrix," *The Journal of Cell Biology*, vol. 109, pp. 317-330 (1989).

Inoue, T., et al., "Effect of the surface geometry of smooth and porous-coated titanium alloy on the orientation of fibroblast in vitro," *Journal of Biomedical Materials Research*, vol. 21, pp. 107-126 (1987).

Jiang, X., et al., "Palladium as a Substrate for Self-Assembled Monolayers Used in Biotechnology," *Anal. Chem.*, vol. 76, pp. 6116-6121 (2004).

Kabat, D., et.al., "Cell Anchorage Determines Whether Mammary Tumor Virus Glycoproteins Are Processed for Plasma Membranes or Secretion," *The Journal of Cell Biology*, vol. 101, pp. 2274-2283 (1985).

Kleinfeld, D., et al., "Controlled Outgrowth of Dissociated Neurons on Patterned Substrates," *The Journal of Neuroscience*, vol. 8, No. 11, pp. 4098-4120(1988).

Lahann, J., et al., "A Reversibly Switching Surface," *Science*, vol. 299, No. 5605, pp. 297-374 (2003).

Lea, A.S., et al., "Manipulation of Proteins on Mica by Atomic Force Microscopy," *Langmuir*, vol. 8, pp. 68-73 (1992).

Lopez, G. P., et al., "Convenient Methods for Patterning the Adhesion of Mammalian Cells to Surfaces Using Self-Assembled Monolayers of Alkanethiolates on Gold," *J. Am. Chem. Soc.*, vol. 115, pp. 5877-5878 (1993).

Mrksich, M., et al., "Using Microcontact Printing to Pattern the Attachment of Mammalian Cells to Self-Assembled Monolayers of Alkanethiolates of Transparent Films of Gold and Silver," *Experimental Cell Research*, vol. 235, pp. 305-313 (1997).

Pale-Grosdemange, C., et al., "Formation of Self-Assembled Monolayers by Chemisorption of Derivatives of Oligo(ethylene glycol) of Structure $HS(CH_2)_{11}(OCH_2CH_2)mOH$ on Gold[1]," *J. Am. Chem. Soc.*, vol. 113, pp. 12-20 (1991).

Patchornik, A., et al., "Photosensitive Protecting Groups," *J. Am. Chem., Soc.*, vol. 92, No. 18, pp. 6333-6335 (1970).

Sigal, GB., et al., "Effect of Surface Wettability on the Adsorption of Proteins and Detergents," *J.Am. Chem. Soc.*, vol. 120, pp. 3464-3473 (1998).

Singhvi, R., et al., "Engineering Cell Shape and Function," *Science*, vol. 264, No. 5159, pp. 696-698 (1994).

Westermark, B., "Growth Control in Miniclones of Human Glial Cells," *Experimental Cell Research*, vol. 111, pp. 295-299 (1978).

Wood, A., "Contact guidance on microfabricated substrta: the response of teleost fin mesenchyme cells to repeating topographical pattern," *Journal of Cell Science*, vol. 90, pp. 667-681 (1988).

Yousaf, M.N., et al., "Turning On Cell Migration with Electroactive Substrates," *Angew. Chem. Int. Ed.*, vol. 40, No. 6, pp. 1093-1096 (2001).

* cited by examiner

METHODS OF ALTERATION OF SURFACE AFFINITIES USING NON-CHEMICAL FORCE-CREATING FIELDS

RELATED APPLICATIONS

This application is a continuation of International Application No. PCT/US2004/002498 filed Jan. 29, 2004, which was published under PCT Article 21(2) in English, and claims priority to U.S. Application Ser. No. 60/443,466, filed Jan. 29, 2003. Both applications are hereby incorporated by reference.

FEDERALLY SPONSORED RESEARCH

This invention was made with U.S. Government support under National Institute of Health Grant No. GM 30367. The Government has certain rights to this invention.

FIELD OF THE INVENTION

This invention generally relates to the alteration of the affinity for an entity of a surface, and in particular, to the alteration of the affinity of the surface by the detachment of molecules therefrom.

DESCRIPTION OF THE RELATED ART

Control over the affinity of a surface for a chemical, biochemical, or biological species is important in many applications, such as drug or cell assays, combinatorial chemistry, and the like. For example, cell adherence on certain substrate surfaces is necessary in many instances for the study of cells in furthering applications such as tissue engineering, biosensors, etc. Cell patterning, i.e., placing cells in discrete portions or regions on a surface, has been facilitated, for example, by photolithography. Although photolithography technology is, in many respects, highly developed, it has several disadvantages. Photolithography utilizes harsh conditions, which can destroy cells. Clean-room facilities and other complex equipment are also typically required and such facilities and equipment are not always readily accessible. Photolithography is also not well suited to controlling the molecular properties of a surface as is required for many sophisticated cell biological experiments. In addition, photolithography typically allows a user to modify a surface only at the beginning of an experiment. Once the cells have been deposited, photolithography cannot typically be used to make further surface modifications.

The adhesion, orientation, spreading, and shape of several cell types have been shown to be affected by topography. For example, to study such properties, cells have been grown on grooved surfaces which have been created by micromachining surfaces or by using photolithography to etch away parts of surfaces. See, for example, D. M. Brunette, *Exp. Cell Res.*, 167:203-217, 1986; T. Inoue, et al., *J. Biomedical Materials Res.*, 21:107-126, 1987; B. Chehroudi, et al., *J. Biomedical Materials Res.*, 22:459-473, 1988; G. A. Dunn and A. F. Brown, *J. Cell Sci.*, 83:313-340, 1986; A. Wood, *J. Cell Sci.*, 90:667-681, 1988; B. Chehroudi, et al., *J. Biomedical Materials Res.*, 24:1203-1219, 1990; P. Clark, et al. *Development*, 99:439-448, 1987.

The viability, growth, proliferation, differentiation, orientation and spreading of certain cells have been shown to depend on the nature of the substrate to which the cells are adhered (see, e.g., D. Gospodarowicz, et al., *Cancer Res.*, 38:4155-4171, 1978; J. Folkman and A. Moscona, *Nature*, 273:345-349, 1978; A. Ben Ze'ev, et al., *Cell*, 21:365-372, 1980; D. E. Ingber, et al., *In Vitro Cell Dev. Biol.*, 23:387-394, 1987; D. E. Ingber and J. Folkman, *J. Cell Biol.*, 109:317-330, 1989). The growth and viability of anchorage dependent cells, for example, may be different when they are allowed to become more extended or flattened, compared to when the cells are maintained in rounded form or in suspension. For example, for fibroblast growth factor ("FGF") stimulated capillary endothelial cells, it has been demonstrated that by altering the density of extracellular matrix ("ECM") attachment sites, the cell shape is altered and the cells may be switched between growth and differentiation modes in vitro (see, D. E. Ingber and J. Folkman, *J. Cell Biol.*, 109:317-330, 1989). It has also been shown that cell-to-cell contact or cell anchorage may affect cellular processes such as post-translational modification of proteins (see, e.g., D. Kabat, et al., *J. Cell Biol.*, 101:2274-2283, 1985).

The study of self-assembled monolayers ("SAMs") is an area of significant scientific research. Such monolayers are typically formed of molecules, each having a functional group that selectively attaches to a particular surface. The remainder of each molecule can interact with neighboring molecules in the monolayer to form a relatively ordered array. Such SAMs have been formed on a variety of substrates, including metals, silicon dioxide, gallium arsenide, and others. SAMs have been applied to surfaces in predetermined patterns in a variety of ways, including via simple flooding of a surface, and through more sophisticated methods such as irradiative patterning.

SAMs may be produced with varying characteristics and with various functional groups at the free end of the molecules which form the SAM, for example, as described in U.S. Pat. No. 5,512,131. Thus, SAMs may be formed which are generally hydrophobic or hydrophilic, generally cytophobic or cytophilic, or generally biophobic or biophilic. Additionally, SAMs with very specific binding affinities can be produced. This allows for the production of patterned SAMs which will adhere cells, proteins, or other biological materials in specific and predetermined patterns. However, controlled or selective alteration of a SAM after it has been formed on a substrate, for example, within a specific region of the substrate, has generally been difficult and/or impractical.

SUMMARY OF THE INVENTION

The present invention generally relates to the alteration of the affinity of a surface by the detachment of molecules therefrom. The subject matter of this application involves, in some cases, interrelated products, alternative solutions to a particular problem, and/or a plurality of different uses of a single system or article.

In one aspect, the invention provides a series of methods. In one set of embodiments, the methods include a step of altering an affinity for an entity of at least a portion of a surface, where the surface has molecules attached thereon, by detaching at a point of attachment at least some of the molecules from the at least a portion of the surface using a non-chemical force-creating field. The methods, in another set of embodiments, include a step of altering, without creating a covalent bond, the affinity for an entity of at least a portion of a surface, where the surface has molecules attached thereon, by exposing at least a portion of the surface to a non-chemical force-creating field. In yet another set of embodiments, the methods include a step of altering the affinity for an entity of at least a portion of a surface, where the surface has molecules attached thereon, by breaking a metal-sulfur bond between at least some of the molecules and the at least a portion of the surface using a non-chemical force-creating field.

In still another set of embodiments, the methods include a step of detaching, at a point of attachment, a plurality of molecules forming a SAM on a surface, by exposing at least a portion of the surface to a non-chemical force-creating field. The methods include, in another set of embodiments, a step of detaching a plurality of molecules forming a SAM on a surface from the surface without creating a covalent bond by exposing at least a portion of the surface to a non-chemical force-creating field. In still another set of embodiments, the methods include a step of exposing a surface to a non-chemical force-creating field wherein at least a portion of the surface is coated with a layer of molecules comprising unmodified ethylene glycol-terminated alkanethiol molecules. In another set of embodiments, the methods include a step of exposing a surface to a non-chemical force-creating field wherein at least a portion of the surface is coated with a layer of molecules comprising unmodified propylene glycol-terminated alkanethiol molecules.

In yet another set of embodiments, the methods include a step of altering an area of a cytophilic region on a surface by exposing the surface to a medium comprising serum and a non-chemical force-creating field. The methods, in still another set of embodiments, include a step of altering an area of a cytophilic region on a surface by exposing the surface to an undefined medium and a non-chemical force-creating field.

In another set of embodiments, the methods include steps of detaching at least a portion of a plurality of molecules attached to a surface of an article by exposing at least a portion of the surface to a non-chemical force-creating field, and detecting migration of the cell with respect to the surface. The article may have a cell attached to the surface and/or to at least some of the molecules attached to the surface in some cases.

The invention, in another aspect, provides a series of devices. In one set of embodiments, the devices comprise an article having a surface, at least a portion of which is coated with a layer of molecules comprising unmodified ethylene glycol-terminated alkanethiol molecules. In another set of embodiments, the devices comprise an article having a surface, at least a portion of which is coated with a layer of molecules comprising unmodified propylene glycol-terminated alkanethiol molecules. In yet another set of embodiments, the devices comprise an article having a surface, at least a portion of which is coated with a layer of molecules comprising alkanethiol molecules comprising ethylene glycol moieties, where the ethylene glycol moieties consist essentially of unmodified ethylene glycol moieties. In still another set of embodiments, the device comprises an article having a surface, at least a portion of which is coated with a layer of molecules comprising alkanethiol molecules comprising propylene glycol moieties, where the propylene glycol moieties consist essentially of unmodified propylene glycol moieties. In some cases, the article can be configured and arranged to be connectable to at least one source of voltage.

In another set of embodiments, the invention provides articles comprising a surface having a first portion and a second portion. The first portion is coated by a SAM comprising molecules having an exposed terminus selected from the group consisting of a hydroxide, an ammonium moiety, a sulfonate, ethylene glycol and propylene glycol. The second portion is coated by a SAM comprising molecules having an exposed hydrophobic and/or cytophilic terminus.

Other advantages, novel features, and objects of the invention will become apparent from the following detailed description of non-limiting embodiments of the invention when considered in conjunction with the accompanying drawings, which are schematic and which are not intended to be drawn to scale. In the figures, each identical or nearly identical component that is illustrated in various figures typically is represented by a single numeral. For purposes of clarity, not every component is labeled in every figure, nor is every component of each embodiment of the invention shown where illustration is not necessary to allow those of ordinary skill in the art to understand the invention. In cases where the present specification and a document incorporated by reference include conflicting disclosure, the present specification shall control.

BRIEF DESCRIPTION OF THE DRAWINGS

Non-limiting embodiments of the present invention will be described by way of example with reference to the accompanying drawings in which.

DETAILED DESCRIPTION

Figure 1A:
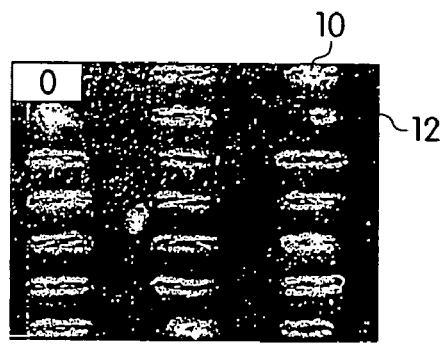
FIGS. 1A-1D are photocopies of a series of photographs of cells on a substrate taken at different times during an experiment, in accordance with one embodiment of the invention.

The present invention provides a series of methods, compositions, and articles for altering a property of a surface (for example, the cytophilicity and/or the hydrophilicity), by exposing at least a portion of the surface to an electric field or other non-chemical, force-creating field and/or force, as explained in more detail below. For embodiments utilizing an electric field, the electric field may be created by any suitable technique, for instance, by applying a voltage across the surface, by electrical induction, etc. In certain embodiments, the surface includes molecules attached thereto that can be detached when exposed to certain force-creating fields, thereby altering the chemical composition of at least a portion of the surface. In one set of embodiments, the molecules attached to the surface may include molecules forming a self-assembled monolayer on the surface. In some embodiments, the molecules attached to the surface may include thiol moieties (e.g., as in an alkanethiol), by which the molecule can become attached to the surface. In certain cases, the molecules may be terminated at the unattached end with one or more hydrophilic groups, for example, unmodified ethylene glycol moieties. In some cases, the molecules attached to the surface may include one or more moieties that can bind to various entities such as proteins, nucleic acids, drugs, cells, etc.

In certain embodiments, non-chemical force-creating fields and/or forces other than the electric fields (e.g., magnetic, electromagnetic, shear, centrifugal, inertial, etc.) can be used to alter the properties of the surface. In the discussion below, reference is typically made to examples in which electric fields are utilized for the detachment of molecules. It should be understood, however, that this is merely for conciseness, and that in other similar embodiments, one or more other non-chemical, force-creating fields and/or forces can be utilized, alone or in combination with an electric field or other fields, for achieving the same or similar purposes and/or results.

The present invention also provides novel methods, devices and techniques useful for controlling the adhesion and/or motility of cells to and/or on specific or predetermined positions on a surface. Such methods, devices, and techniques can be useful in a wide array of cellular biology applications, for example, cell culturing, cell motility assays, recombinant protein production, drug screening, cytometry, toxicology, cell screening, microinjection, immobilization of cells, influencing the state of differentiation of a cell including promoting differentiation, arresting differentiation, or causing dedifferentiation, etc. The methods, devices, and techniques of the invention could also potentially be useful in the creation of artificial tissues, or in connection with creating artificial organs such as artificial liver devices. Additionally, the devices and techniques described could also potentially be useful in connection with generating surfaces useful in relation to prosthetic or implantable devices.

As used herein, "affinity" refers to the degree and strength of attraction between a first entity (e.g., a molecule) and a second entity, which is reflective of the propensity of the first entity to attach to the second entity when the first and second entity are in proximity with each other. Thus, as used herein, a molecule having affinity for an entity is able to attach to and, in some cases, bind to the entity. The molecule may be able to attach to the entity by any suitable mechanism, for example, a physical mechanism, such as physical adsorption, charge interactions, hydrophobic effects, van der Waals interactions, electrostatic attraction, magnetic attraction, molecular intercalation, etc., and/or via bond-forming mechanisms, such as chemisorption, covalent bond formation, hydrogen bond formation, and the like. An "attached" molecule, as used herein, refers to one that is sufficiently immobilized with respect to a surface or other entity such that it will not detach under typical conditions of use (i.e., by fluid movement or thermal energy), without exposure to an electric field and/or other source of force selected to cause detachment of the molecules. A "bond," as used herein in this context, broadly refers to any physical and/or chemical attractive interaction between a first entity, such as a molecule, and another entity, such as the surface of the substrate, where the force of the attractive interaction is of the magnitude of chemical bond forces and is generally sufficient to allow the first entity to become immobilized with respect to the other entity. Some examples of such "bonds" include, without limitation, a covalent bond, a coordinated bond, chemisorption (e.g., a metal-sulfur bond), hydrogen bonding, and the like. The affinity may also be characterized as cytophilic and/or cytophobic in nature, as further described below.

As described herein, the application of an electric field to at least a portion of a substrate according to certain embodiments of the invention can cause molecules attached to at least a portion of the substrate to detach. The molecules attached to the substrate may be hydrophilic or hydrophobic in some cases, or the molecules may have an affinity to another entity, as described above. In some cases, the substrate may include more than one type of molecule thereon that can be detached. For example, the substrate may include a first type of molecule that detaches when the substrate is exposed to a first electric field strength and/or duration, (or other non-chemical force-creating field) and a second type of molecule that does not detach when the substrate is exposed to the first electric field strength and/or duration, but is able to detach when the substrate is exposed to a second electric field strength and/or duration greater than the first electric field strength and/or duration.

In some embodiments of the invention, the molecule(s) may be detached from the surface of the substrate in its (their) entirety, e.g., without internal reaction or rearrangement. That is, under the influence of an electric field, the molecule detaches from the substrate at its point of attachment to the substrate, for example, such that there is no rearrangement or other structural changes internally of the molecule (i.e., the detached molecule is essentially structurally the same as when it was attached to the surface of the substrate). As used herein, a molecule "detached at its point of attachment" to a surface means that, for a molecule connected to the surface by a specific attractive interaction (e.g., a bond as further described herein), the specific attractive interaction connecting the molecule to the surface is disrupted (e.g., a bond is cleaved or severed), thereby disconnecting the molecule from the surface. As one specific non-limiting example, in an alkanethiol bound to a gold surface via a gold-thiol bond, cleavage of the molecule from the surface at the gold-sulfur bond will result in a molecule that is detached at its point of attachment to the surface. In contrast, reactions where only a portion of the molecule is released, i.e., reactions where a portion of the molecule remains bound to the surface afterwards, do not result in molecules detached at the point of attachment as defined herein. Thus, in the above example of an alkanethiol bound to a gold surface through a gold-thiol bond, a cleavage or a rearrangement of other bonds within the alkanethiol that causes a portion of the alkanethiol to detach (for example, through the breaking of a carbon-carbon bond or a carbon-oxygen bond) will not result in a molecule that is detached at its point of attachment.

In another embodiment of the invention, the molecules are detached from the surface under the influence of an electric field without the formation or rearrangement of covalent bonds within the molecule. In yet another embodiment, the molecule may be detached from the surface by the detachment of a chemisorbed species under the influence of the electric field, for example, a molecule may be detached from a surface through the detachment of a metal-sulfur bond, for instance, where the molecule includes a thiol, sulfide or disulfide at the point of attachment that interacts with a metal on the surface. In some cases, the molecule being detached may be a SAM-forming molecule.

As used herein, an "electric field" is given its ordinary meaning, i.e., an electrostatic field. The electric field may be constant or steady with respect to time, or the electric field may vary with respect to time in some manner, for example, in a sinusoidal manner, or in a series of pulses (e.g., as produced by a series of electrical pulses). The electric field that the substrate is exposed to in certain embodiments may be created by any suitable technique, for example, by electrodes that are externally connected to the substrate, through metal portions of the substrate (for example, through gold channels, plates or regions within the substrate, through microelectronic channels etched on the substrate, etc, or the like). One non-limiting example of such a technique is given below in Example 1 with reference to FIG. 1E. In some embodiments, for instance, where at least a portion of a substrate contains one or more molecules attached thereon, the electric field that the substrate is exposed to may be of sufficient magnitude and/or duration such that the electric field is able to cause detachment of at least some of the molecules attached to the substrate or portion thereof (e.g., detachment of SAM-forming molecules attached to the substrate). In some instances, the molecules may be detached from the substrate without detaching or damaging certain other entities present on the surface of the substrate, for example, proteins, cells, other SAM-forming molecules located on other portions of the substrate, etc.

In some embodiments, a specific portion or region of the substrate may be exposed to an electric field sufficient to detach molecules in that portion or region. In certain cases, one portion of the surface is exposed to the electric field at field intensities and/or durations sufficiently large enough to cause detachment of certain molecules from the surface at that portion of the surface, but at field intensities and/or durations insufficient to cause detachment of molecules or other undesirable effects on other portions of the substrate, i.e., those portions which are not exposed to the electric field. For example, in an embodiment in which a surface having viable cells thereon is exposed to an electric field, as described in more detail below, the electric field intensity and/or duration may be less than the electric field intensity and/or duration necessary to cause hydrolysis of water, electroporation of cells, etc. In some embodiments, the electric field intensity (or the RMS electric field intensity if the electric field is a time-varying electric field, e.g., a sine wave) may be less than about 1 kV/m (e.g., less than about 10 V across a distance of 10 mm between two electrodes), and in certain embodiments less than about 500 V/m, or less than about 300 V/m. In other embodiments, the electric field intensity may be at least about 50 V/m, in certain embodiments at least about 100 V/m, in certain embodiments at least about 140 V/m, in certain embodiments at least about 200 V/m or more. In some cases, the electric field intensity may be between about 50 V/m and 500 V/m, in other cases between about 100 V/m and about 300 V/m, in other cases between about 140 V/m and about 200 V/m, in other cases between about 200 V/m and about 1 kV/m, in other cases between about 100 V/m and about 200 V/m, and in still other cases between about 50 V/m and about 100 V/m.

For molecular detachment by electric field exposure, in one set of embodiments, the substrate may be exposed to the electric field for any suitable length of time necessary to cause detachment of molecules that are desired to be detached from the substrate, preferably without also causing undesirable effects (for instance, the detachment of other molecules). For example, in certain embodiments, the substrate may be exposed to an electric field for at least about 5 seconds, at least about 10 seconds, at least about 15 seconds, at least about 30 seconds, or at least about 1 minute or more in some cases. In certain embodiments, the substrate may be exposed to the electric field for less than about 10 minutes, in some cases in less than about 5 minutes, and in other cases in less than about 2 minutes. In some cases, the substrate may be exposed to the electric field for between about 5 seconds and about 3 minutes, in other cases between about 10 seconds and about 2 minutes, in other cases between about 30 seconds and about 1 minute, and in still other cases between about 10 seconds and about 1 minute.

Given the teaching and guidance provided herein, those of ordinary skill in the art will be able to select methods of determining proper suitable electric field intensities and/or proper application times for a particular system and use. As one non-limiting example of a suitable screening test for determining appropriate parameters, a substrate having one or more SAMs attached thereon may be exposed to a range of electric field intensities and/or application times to determine the electric field intensities and/or times sufficient to cause detachment of at least some of the molecules forming the SAM in at least a portion of the substrate of that particular system. The electric field intensity and/or the exposure time of the electric field can be systematically varied to find optimal values for the particular molecules (e.g., SAM-forming molecules, etc.) being tested, and/or to find which of various molecules can be detached in response to an electric field having particular characteristics. In some embodiments, particular molecules (e.g., SAM-forming molecules, etc.) can be labeled with a detectable molecule or entity to facilitate detection. Suitable methods of detecting the detachment of molecules (e.g., those forming a SAM) from the surface include, without limitation, the detection of fluorescent or radioactive molecules or molecules bound to a fluorescent or radioactive marker, measurement of molecular concentrations in solution (e.g., through laser light scattering, HPLC, viscosity measurements, etc.), detection of changes in surface properties of the substrate (e.g., by contact angle measurements, surface plasmon resonance, electrical measurements such as cyclic voltammetry, etc.), or the like. Similarly, in embodiments where non-chemical force-creating fields and/or forces are used that are or include those other than electric fields, similar screening tests as applied above can be utilized to determine the appropriateness of a particular non-chemical, force-creating field and/or force for the detachment of particular molecules and/or the intensity and/or duration, or the combination of such fields and/or forces, that are necessary for achieving a desired result.

As mentioned above and described in more detail below, certain embodiments of the invention involve surfaces with SAMs attached thereon. As used herein, the term "self-assembled monolayer" (SAM) refers to a relatively ordered assembly of molecules attached on a surface, in which the molecules are oriented approximately parallel to each other and roughly perpendicular to the surface. The molecules may be attached to the surface through a bond, for example, a metal-sulfur bond.

A SAM-forming molecule may be attached to the substrate by any of a wide variety of suitable mechanisms known in the art that result in stable SAM formation on the substrate. For example, in one series of embodiments, the substrate and SAM-forming compound are selected such that the SAM-forming compound terminates at a first end in a functional group that attaches to, and typically binds to, a surface of the substrate. As used herein, the terminology "end" of a compound includes both the physical terminus of a molecule as well as any portion of a molecule available for forming a bond or other attachment with the substrate in a way that the compound can form a SAM on the substrate. The compound may comprise, for example, a molecule having first and second terminal ends, separated by a spacer portion, the first terminal end comprising a first functional group selected to bond to the surface of the substrate, and the second terminal end optionally including a second functional group selected to provide a SAM on the substrate that has a desirable exposed functionality, and/or a functionality that can be reacted to produce a desirable exposed functionality, as further described below. The spacer portion of the molecule may be selected to provide a particular thickness of the resultant SAM, and/or to facilitate SAM formation. Although SAMs of the present invention may vary in thickness, e.g., as further described below, SAMs having a thickness of less than about 50 Angstroms, less than about 30 Angstroms or less than about 15 Angstroms may be particularly useful in certain instances. These dimensions are generally dictated by the selection of the SAM-forming compound and in particular the spacer portion thereof, and can be readily selected and/or prepared by those of ordinary skill in the art.

The SAM-forming molecule, in some embodiments, may also include a spacer portion that interacts with neighboring molecules in the monolayer to form a relatively ordered array. The spacer functionality of the SAM-forming compound may connect a functional group able to bind or otherwise attach to the substrate with an exposed functional group at a second end of the molecule, as further described below. Alternately, a portion of the spacer may form the exposed functional group. Any spacer that does not substantially and undesirably disrupt SAM packing is potentially suitable. The spacer may, in specific embodiments, be, for example, polar; non-polar; halogenated or, in particular, fluorinated; positively charged; negatively charged; or uncharged. As additional examples, a saturated or unsaturated, linear or branched alkyl, aryl, or other hydrocarbon spacer may be used in certain embodiments of the SAM-forming compound.

A variety of lengths of SAM-forming compounds can potentially be employed in the present invention. If two or more different SAM-forming compounds are used, it is sometimes advantageous that these species have similar lengths. However, in certain embodiments, for example when a two or more step process is used, in which a first SAM is provided on a surface and at least a second SAM is provided on the surface, the various SAMs being continuous or noncontinuous, it may be advantageous in some circumstances to select molecular species for the formation of the various SAMs that have different lengths. For example, if the SAM initially formed has a first molecular length and the SAM subsequently derivatized to the surface has a second molecular length greater than that of the first molecular length, a continuous SAM having a plurality of "wells" may result. These wells are the result of the first SAM being surrounded by the second SAM having a longer chain length. Such wells may be advantageously fabricated according to certain embodiments, for example, when it is desirable to add greater lateral stability to particular biological materials, such as cells, which have been captured in the wells. Such wells may also form the basis for reaction vessels.

Methods that can be used to form a SAM are well known and are described in, for example, U.S. Pat. No. 5,620,850, which is hereby incorporated by reference. See also, for example, Laibinis, P. E., Hickman, J., Wrighton, M. S., Whitesides, G. M., *Science,* 245:845, 1989; Bain, C., Evall, J., Whitesides, G. M., *J. Am. Chem. Soc.,* 111:7155-7164, 1989; Bain, C., Whitesides, G. M., *J. Am. Chem. Soc.,* 111:7164-7175, 1989, each of which is incorporated herein by reference. In some cases, the SAM can be made up of SAM-forming species that form SAMs on surfaces, and/or those species in combination with other species able to participate in a SAM. In some embodiments, some of the species that participate in the SAM include a functionality or group able to bind, optionally covalently, to a surface, such as a thiol functionality which will chemisorb to a gold surface.

The SAM-forming compound may terminate in a second end, generally opposite to the end bearing the functional group selected to bind to the surface material. The second end can comprise any of a variety of exposed functionalities. For example, in one embodiment of the invention, at least some of the SAM-forming molecules forming a SAM have a structure:

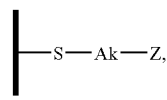

where ▌ represents the substrate, Ak comprises an alkyl group and Z comprises an exposed functional group, e.g., a moiety able to bind to an entity such as a cell or a protein. As discussed above, the bond connecting S to the substrate may be any bond capable of immobilizing the SAM-forming molecule to the surface, for example, a chemisorption bond such as a gold-sulfur bond.

As used herein, an "alkyl" is given its ordinary meaning as used in the field of organic chemistry. Alkyl or aliphatic groups useful or potentially useful for practicing the invention can contain any of a wide number of carbon atoms, for example, between 1 and 20 carbon atoms, between 1 and 15 carbon atoms, or between 1 and 10 carbon atoms. In some embodiments, the alkyl may have at least 2 carbon atoms, in other embodiments at least 3 carbon atoms, in other embodiments at least 11 carbon atoms, in other embodiments at least 13 carbon atoms, and in other embodiments at least 18 carbon atoms. In certain embodiments, the alkyl may have between 11 and 18 carbon atoms inclusive or between 13 and 18 carbon atoms inclusive. In one set of embodiments, the alkyl may be an undecyl, a dodecyl, a tridecyl, a tetradecyl, a pentadecyl, a hexadecyl, a heptadecyl, or a octadecyl moiety. Typically, an alkyl group is a non-cyclic structure. The carbon atoms may be arranged in any permissible configuration within the alkyl moiety, for example, as a straight chain or a branched chain (including multiple branches). The alkyl moiety may contain only single bonds, or alternatively, may contain one or more double or triple bonds within its structure, for example, as in an alkene, an alkyne, an alkadiene, an alkadiyne, an alkenyne, etc. The alkyl moiety may also contain one or more substituents in some embodiments. For example, in certain embodiments, the alkyl group may contain a halogen, an alkoxy (e.g., methoxy or ethoxy), an amine (e.g., a primary, secondary, or tertiary amine), or a hydroxide as a substituent. If more than one substituent is present, then the substituents may be the same as or different from each other.

In some cases, the exposed functional group Z may be an exposed functional group that confers a specific property to the SAM-forming molecule. That is, the compound may include an exposed functionality that, when the compound forms a SAM on the surface material, is able to confer upon the surface a specific property, such as an affinity for a particular entity or entities. For example, in certain non-limiting embodiments, Z can be a cytophilic moiety, a cytophobic moiety, a biophilic moiety, a biophobic moiety, a hydrophilic moiety, a hydrophobic moiety, a chelating group, an antibody, a peptide or protein sequence, a nucleic acid sequence, an affinity tag (e.g., a member of a biotin/avidin or biotin/streptavidin binding pair), or a moiety that selectively binds various biological, biochemical, or other chemical species, etc.

In some embodiments, Z may be, for example, ionic, nonionic, polar, nonpolar, halogenated, alkyl, or aryl. A non-limiting, exemplary list of functional groups that Z could comprise include: —OH, —CONH—, —CONHCO—, —NH$_2$, —NH—, —COOH, —COOR, —CSNH—, —$NO_2^-$—, —$SO_2^-$—, —RCOR—, —RCSR—, —RSR, —ROR—, —$PO_4^{-3}$, —$OSO_3^{-2}$, —$COO^-$, —$SOO^-$, —RSOR—, —$CONR_2$, —$CH_3$, —$PO_3H^-$, -2-imidazole, —$N(CH_3)_2$, —$NR_2$, —$PO_3H_2$, —CN, —$(CF_2)_n$— $CF_3$ (where n=1-20 inclusive, and preferably 1-8, 3-6, or 4-5), olefins, and the like. In addition to these, those mentioned above as forming part of the example SAM-forming molecules can also be used more generally. In the above list, R is hydrogen or an organic group such as a hydrocarbon or an alkyl. As used herein, the term "hydrocarbon" includes alkyl, alkenyl, alkynyl, cycloalkyl, aryl, alkaryl, aralkyl, and the like. The hydrocarbon group may, for example, comprise methyl, propenyl, ethynyl, cyclohexyl, phenyl, tolyl, and benzyl groups. The term "fluorinated hydrocarbon" is meant to refer to fluorinated derivatives of the above-described hydrocarbon groups.

In another set of embodiments, Z may comprise a moiety:

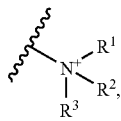

where $R^1$, $R^2$, and $R^3$ are each independently a hydrogen or an organic group such as a hydrocarbon or an alkyl, such as methyl, ethyl, propyl, butyl, isopropyl, etc. In still another set of embodiments, Z may comprise a sulfonate group (—$SO_3^-$).

In one set of embodiments, Z may comprise polyethylene glycol ("PEG") and/or polypropylene glycol ("PPG") moieties, e.g., moieties having the general formula —$(OCH_2CH_2)_n$— or —$(OCH_2CH_2CH_2)_n$—, respectively, where n is any number of repeat units that gives the SAM-forming molecule, when the SAM-forming molecule is formed into a SAM on a surface, a desirable surface characteristic, such as cytophobicity or biophobicity, as those terms are further defined herein. The actual number of repeat units in the SAM-forming molecules utilized can be determined by those of ordinary skill in the art, depending on the specific application, using routine experimentation. In certain embodiments, the functional group may include various combinations of polyethylene glycol and polypropylene glycol repeat units (including block and/or alternating combinations). In some cases, some or all of the polyethylene glycol and/or polypropylene glycol repeat units are substantially unmodified, i.e., the units have the general formula —$(OCH_2CH_2)_n$—OH and/or —$(OCH_2CH_2CH_2)_n$—OH, respectively. In certain cases n can be between 1 and 20 inclusive, in certain embodiments between 1 and 10 inclusive, in certain embodiments between 1 and 8 inclusive, and in certain embodiments 4 or 5, or between 3 and 6 inclusive.

In the embodiments described herein involving SAMs formed of SAM forming molecules having an exposed functional group (i.e. a Z group), the SAMs may be formed that comprise molecules having a particular exposed functional group, the SAMs may be formed that consist essentially of molecules having a particular exposed functional group, or the SAMs may be formed that consist of molecules having a particular exposed functional group. In certain embodiments, SAMs may be formed comprising a plurality of molecules providing a plurality of different exposed functional groups.

In one set of embodiments, the exposed functional group may be chosen from a wide variety of compounds or fragments thereof which will render the SAM generally or specifically "biophilic" as this term is defined below. "Generally biophilic" functional groups are those that would have a tendency to promote the binding, adherence, or adsorption of biological materials such as, for example, intact cells (e.g., "cytophilic" functional groups), fractionated cells, cellular organelles, proteins, lipids, polysaccharides, simple carbohydrates, complex carbohydrates, nucleic acids, etc. Generally biophilic functional groups can include hydrophobic groups or alkyl groups with charged moieties such as $COO^-$, $PO_3H^-$, or 2-imidazolo groups, and/or compounds or fragments of compounds such as extracellular matrix proteins, fibronectin, collagen, laminin, serum albumin, polygalactose, sialic acid, peptide sequences such as RGD, antibodies, and various lectin binding sugars. "Specifically biophilic" functional groups are those that selectively or preferentially bind, adhere or adsorb a specific type or types of biological material so as, for example, to identify and/or isolate the specific material from a mixture of materials. Specifically biophilic materials include antibodies or fragments of antibodies and their antigens, cell surface receptors and their ligands, nucleic acid sequences and many others that are known to those of ordinary skill in the art. The choice of an appropriate biophilic functional group depends on considerations of the biological material sought to be bound, the affinity of the binding required, availability, ease of use, effect on the ability of the SAM-forming compound to effectively form a SAM, and cost. Such selection is within the knowledge, ability and discretion of one of ordinary skill in the art.

In another set of embodiments, the exposed functional group may be chosen from a wide variety of compounds or fragments thereof which will render the SAMs "cytophilic," that is, adapted to promote cell attachment. Molecular entities creating cytophilic surfaces are well known to those of ordinary skill in the art and include antigens, antibodies, cell adhesion molecules, extracellular matrix molecules such as laminin, fibronectin, synthetic peptides, carbohydrates, peptide sequences such as RGD, and the like.

In another set of embodiments, the exposed functional group may be chosen from a wide variety of compounds or fragments thereof which will render the SAM "biophobic" as that term is defined below. "Biophobic" SAMs are those with a generally low affinity for binding, adhering, or adsorbing biological materials such as, for example, intact cells, fractionated cells, cellular organelles, proteins, lipids, polysaccharides, simple carbohydrates, complex carbohydrates, and/or nucleic acids. Biophobic functional groups can include polar but uncharged groups including unsaturated hydrocarbons. In certain embodiments, biophobic functional groups can include hydrophilic groups, such as the polyethylene glycol and/or polypropylene glycol moieties previously discussed.

In yet another set of embodiments, the functional groups may be chosen from a wide variety of compounds or fragments thereof which will render the SAM "cytophobic," i.e., such that the SAM has a generally low affinity for binding, adhering, or adsorbing cells. Molecular entities known to create cytophobic surfaces can be selected by those of ordinary skill in the art and include, for example, but not limited to, those groups mentioned above as being biophobic, such as uncharged functional groups such as unsaturated hydrocarbons, or polyethylene glycol groups, etc.

In certain embodiments, the functional groups may be chosen to render the SAM-coated surface hydrophobic and/or hydrophilic. As used herein, the terms "hydrophobic" and "hydrophilic" are given their ordinary meaning as used in the art. In certain cases, a hydrophilic surface may also be cytophobic and/or biophobic, while a hydrophobic surface may also be, in some cases, cytophilic and/or biophilic. The degree of hydrophilicity of a hydrophilic and/or a hydrophobic surface can be readily determined and controlled via proper selection of SAMs bearing particular expressed functional groups as determined through no more than routine experimentation by those of ordinary skill in the art, for example, by using contact angle measurements, determining the water/oil partition coefficient of the molecules and/or the functional groups that comprise the SAM, etc. In some cases, the terms "hydrophobic" and "hydrophilic" are defined relative to each other, where the hydrophilic entity has a greater affinity to water than does the hydrophobic entity.

In addition, in certain embodiments, exposed functional groups comprising an affinity tag may be employed. The term "affinity tag" is given its ordinary meaning in the art. An affinity tag is any biological or chemical material that can readily be attached to a target biological or chemical material. Affinity tags may be attached to a target biological or chemical molecule by any suitable method known in the art. For example, in some embodiments, the affinity tag may be attached to a target nucleic acid sequence using a nucleic acid sequence complementary to the target nucleic acid sequence. As another example, an affinity tag such as biotin may be chemically coupled, for instance covalently, to a target protein or peptide, by allowing binding of biotin to an avidin and/or streptavidin moiety fastened with respect to the target protein or peptide.

Non-limiting examples of SAM-forming molecules having the above-described structure which are useful or potentially useful in certain embodiments of the invention include, but are not limited to, the following molecules (n in certain embodiments can be between 1-20 inclusive, and, in some cases, n can be between 3 and 6 inclusive, or 4 and 5):

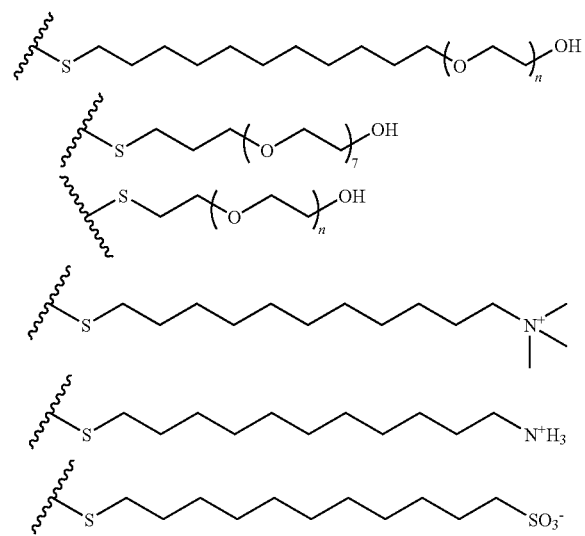

As is apparent from the description above, a wide variety of surface materials and SAM-forming compounds are potentially suitable for use in the context of the present invention. Those of ordinary skill in the art will be able to readily select suitable materials and suitable SAM-forming compounds, based on desired properties and affinities for a particular application, using no more than routine optimization and experimentation. A non-limiting example list of combinations of surface materials and functional groups which will bind to those surface materials follows. Any and all such combinations are within the scope of the present invention but the invention is not limited to these. Preferred materials for use as the surface material and/or substrate include various metals such as gold, silver, copper, cadmium, zinc, palladium, platinum, mercury, lead, iron, chromium, manganese, tungsten, and/or any alloys or combinations of the above, e.g., when employed with sulfur-containing functional groups such as thiols, sulfides, disulfides, or the like; semiconducting materials such as doped silicon employed with silanes and/or chlorosilanes; platinum and/or palladium employed with nitrites and/or isonitriles; and copper employed with hydroxamic acids. Additional suitable functional groups for binding to certain surfaces can include acid chlorides, anhydrides, sulfonyl groups, phosphoryl groups, hydroxyl groups and amino acid groups. Additional surface materials can include other semiconducting materials, such as germanium and/or Group III-V compounds (e.g., GaAS, InAs, GaP, InP, GaN, etc.). According to one set of embodiments, a combination of gold and/or palladium as the surface material or substrate and a SAM-forming compound having at least one sulfur-containing functional group such as a thiol, sulfide, or disulfide is selected.

The surface material of the substrate may comprise the entire substrate onto which the patterned SAMs of the present invention are bonded or otherwise attached, or may be a thin film deposited upon an article. Where a separate substrate is used, it may comprise any of a wide variety of biological, non-biological, organic, or inorganic materials, or a combination of any of these existing as particles, strands, precipitates, gels, sheets, tubing, spheres, containers, capillaries, pads, slices, films, slides, plates, etc. In certain embodiments, the substrate of the present invention is substantially planar, although it need not be according to other embodiments. The substrate may be formed of a conductive material, a semiconducting material, and/or non-conducting material, and may comprise, for example, alumina, plastic or other organic polymers including acrylonitrile-butadine-styrene copolymers, polysulfone, metals and/or any of the above materials described with respect to the surface material of the present invention. The substrate may additionally include a bonding layer, for example a thin titanium film, to promote adhesion between the surface material and the substrate.

The surface material, for embodiments involving coated substrates, is generally of a thickness on the order of 500 microns, but may be substantially thicker or may be substantially thinner. For example, when a substrate as a base material is employed, the surface material may have a thickness of less than about 100 nanometers, less than about 10 nanometers, or even less than about 6 nanometers. When a thin film of surface material is employed, and a transparent substrate supports the surface material, a transparent base support for a SAM can result, and this may be advantageous in standard light or electron microscopic or spectrophotometric detection or analysis of any biological material interacting with a SAM on the surface material.

In certain sets of embodiments, SAMs formed on a substrate surface may be modified after formation for a variety of purposes. For example, a SAM-forming compound on a substrate may have an exposed functionality including a protecting group which may be removed to effect further modification of the SAM. For instance, a photoremovable protecting group may be used, where the group is advantageously selected such that it may be removed without disturbance of the SAM of which it is a part. For example, a protective group may be selected from a wide variety of positive light-reactive groups, for example, nitroaromatic compounds such as o-nitrobenzyl derivatives or benzylsulfonyl. Photoremovable protective groups can be readily selected by those of ordinary skill in the art and are described in, for example, U.S. Pat. No. 5,143,854, issued Sep. 1, 1992; Patchornik, *J. Am. Chem. Soc.*, 92:6333, 1970; or Amit, et al., *J. Org. Chem.*, 39:192, 1974, all of which are incorporated herein by reference. Alternatively, a reactive group may be provided on an exposed portion of a SAM that may be activated or deactivated by electron beam lithography, x-ray lithography, or any other suitable type of radiation exposure. Such protections and deprotections of exposed functional groups may aid in chemical or physical modification of an existing surface-bound SAM, for example in lengthening existing molecular species forming the SAM, for example, as described in U.S. Pat. No. 5,143,857, incorporated herein by reference.

As a specific example, when only a subset of cells in a sample are desired to be immobilized to an article of the invention, for example, the white blood cells in a blood sample containing both red and white blood cells, a specifically biophilic SAM may be chosen that will selectively bind the cells of interest and, subsequent to binding, the extraneous cells may be washed away. Given a particular set or subset of cells to be studied, the choice of a biophilic SAM specific to those cells is within the ability of one of ordinary skill in the art and, given the disclosures herein, one of ordinary skill in the art is enabled to produce appropriate patterned biophilic SAMs specific for those cells.

Many methods may be used to apply and attach the SAM-forming molecules to a substrate surface. For example, the SAM-forming molecules may be applied to the substrate by stamping or micropatterning techniques, organic synthesis techniques, and the like. A variety of suitable methods to attach the SAM to the substrate are known in the art and may be chosen by one of ordinary skill in the art to suit a particular purpose.

For example, in one set of embodiments, the SAM-forming molecules may be patterned on the substrate using a stamp in a "printing" process in which the "ink" consists of a solution including a SAM-forming compound capable of attaching to a surface to form a SAM. The ink is applied to the surface of a substrate using the stamp and deposits a SAM on the substrate in a pattern determined by the pattern on the stamp. The substrate may be stamped repeatedly with the same or different stamps in various orientations and with the same or different SAM-forming solutions. In addition, after stamping, portions of the substrate which remain uncovered by SAMs may optionally be derivatized using any suitable technique known in the art, for example, exposure of the uncovered portions to another solution containing a SAM-forming compound. The SAM-forming or derivatizing solutions can be chosen such that the regions of the finished substrate defined by the patterns differ from each other in their ability to bind to materials such as biological or biochemical materials (e.g., proteins, drugs, cells, etc.). As one example, cytophobic SAM-forming compounds may be patterned on a cytophilic substrate to create a pattern of cytophobic SAMs and cytophilic regions not containing SAMs (or, alternatively, containing cytophilic SAMs), such that certain cells applied to the substrate can bind to the cytophilic regions, but are unable to bind to regions containing the SAMs; thereafter, application of a suitable electric field to the substrate, or to portions of the substrate, may detach the SAMs from the substrate or those in those portions subjected to the field, permitting the cells to then migrate into those portions where the SAMs have been detached.

In certain embodiments, the stamp described above may be formed via a molding process. The mold used to form the stamp may be a commercially available item such as a transmission electron microscopy grid or any other corrugated material possessing a pattern which is desired to be reproduced on the stamp, or a mold especially prepared by any of a variety of methods known in the art. The stamp may be produced by casting a material, e.g., a polymer such as a silicon polymer (e.g., polydimethylsiloxane) onto a mold having the desired pattern. Various techniques for forming stamps for patterning SAMs are known in the art and several are described in detail in, for example, U.S. Pat. No. 6,368,838, by Singhvi, et al., entitled "Adhering Cells to Cytophilic Islands Separated by Cytophobic Regions to form Patterns and Manipulate Cells," hereby incorporated by reference, to which the reader is referred to for more details.

As mentioned above, in some embodiments, after a desired SAM pattern has been formed on the substrate by stamping, the portion of the substrate which is bare or not covered by the stamped SAM may be further reacted or otherwise processed, for example, to add chemical functionality thereto, or to add one or more additional regions containing SAMs. For example, the portion of the substrate which is not covered by the stamped SAM may, in some cases, be derivatized by exposing it to a second or "filling" solution with characteristics differing from the first solution which was used as the ink for forming the initial stamped pattern. This exposure may be accomplished using stamping techniques similar to those previously described, by dipping the substrate in a bath of solution, by pouring the solution onto the substrate, or by any other convenient method which preferably does not disrupt the patterned SAM. The second solution in certain embodiments may form a SAM over the surface of the plate which is not already covered by the patterned SAM of the ink. That is, the second of filling solution may contain a second SAM-forming compound which will form a second or "filling" SAM on the bare portions of the substrate. The result of such an embodiment can be a plate essentially completely covered by complementary patterns of two or more SAMs of differing properties. As an example, two SAM-forming compounds able bind different cell types may be patterned on a substrate such that one SAM region is able to bind a first cell type and a second SAM region separate from the first region is able to bind a second cell type; application of an electric field to the substrate may then cause selective detachment of one of the SAMs, and consequently, selective detachment of only one of the cell types.

Of course, it is not necessary in all embodiments to derivatize or otherwise react or coat any bare portions of the surface remaining after forming patterned SAMs. Depending upon the surface used, the bare surface may have the desired biophilic or biophobic characteristics and, thus, any additional steps may be omitted. For example, when it is desired that cells adhere to a portion of a surface, exposure of the bare surface to a medium containing serum may be sufficient to facilitate binding of the cells.

In certain embodiments, the substrate may be patterned such that one or more regions on the surface are able to bind cells and/or other entities, while a second region on the surface is unable to bind the cells and/or other entities; exposure of the second region to an electric field may then change the affinity of the second region (e.g., by detaching SAM-forming molecules at their point of attachment to the surface) so as to allow the second region to then bind the cells and/or the other entities. The regions may be distributed in any suitable pattern on the surface, for example, half of the substrate may be cytophilic and/or biophilic, while the other half of the substrate may be cytophobic and/or biophobic. In another embodiment, the two or more regions may be distributed such that one or more regions forms channels or isolated islands within another region. As used herein, an "island" is a contiguous region adapted to bind to a particular entity or class of similar entities, such as cells and/or other entities generally, or a particular type of cell or type of entities.

For example, as shown in FIG. 1A, the substrate may have individual cytophilic islands 10 surrounded by cytophobic region 12, or vice versa. In some embodiments, the regions may be such that one cell type is able to bind to a first region, but not a second region, while a second cell type different from the first cell type is able to bind to the second region but not the first region. The nature of the patterning of the two or more regions on the surface will be dependent on the specific application for which the substrate is employed (e.g., a drug assay, cell migration/function assay, etc.), and can be readily selected by those of ordinary skill in the art for a wide variety of purposes. For example, if an island size roughly commensurate with the projected size of cells when bound is desired, it is well within the ability of one of ordinary skill in the art to vary the island size to determine a size appropriate to the intended use without undue experimentation. This is most easily accomplished by beginning with a plate bearing "islands" of varying sizes, contacting the plate with a suspension of cells, and then determining which size or sizes of islands appropriately bound cells. In one embodiment, the size of the islands is chosen such that it is not so large as to admit binding of more than one cell per island.

Figure 6A:
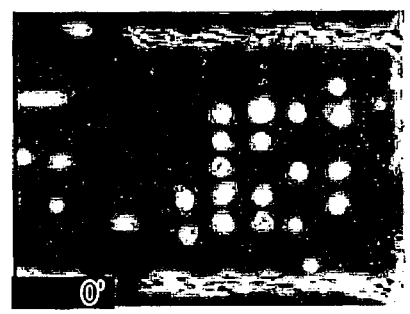
FIGS. 6A-6L are photocopies of a series of photographs of the release of various cell types from confined patterns, in accordance with one embodiment of the invention.
Figure 6B:
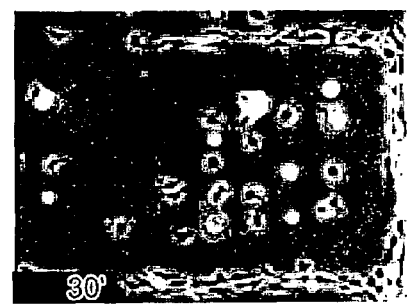
Figure 6C:
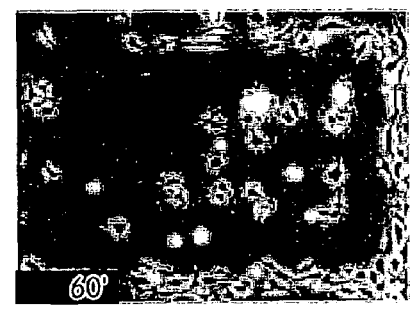
Figure 6D:
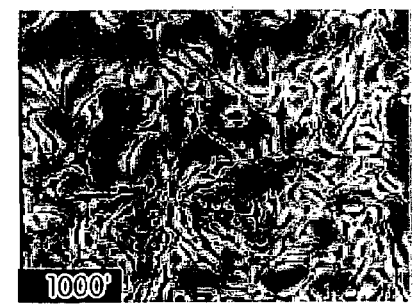
Figure 6E:
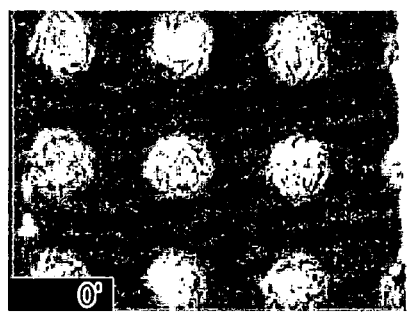
Figure 6F:
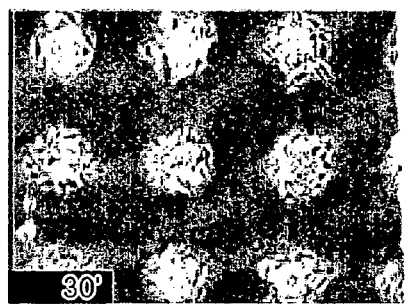
Figure 6G:
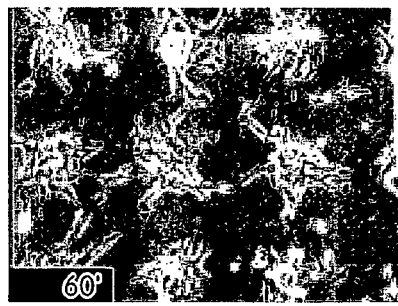
Figure 6H:
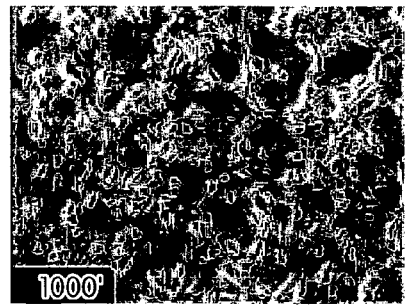
Figure 6I:
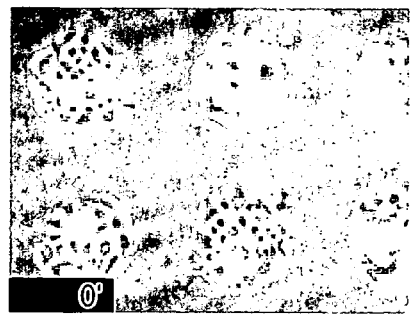
Figure 6J:
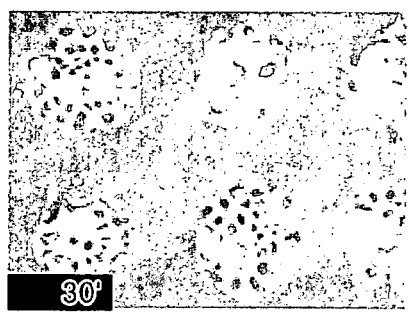
Figure 6K:
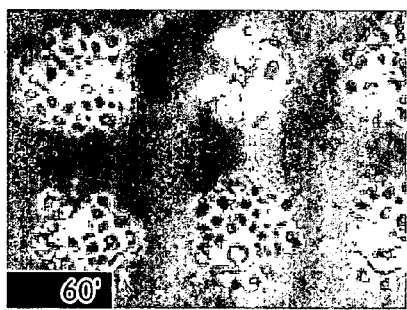
Figure 6L:
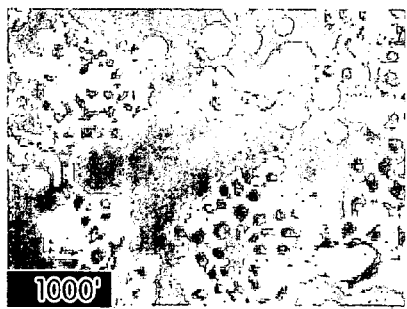

Cytophilic islands, for certain embodiments involving cell binding to SAMs, can take on virtually any shape when manufactured according to the methods of the invention, including rectangular shapes, elongated shapes (e.g., as illustrated in FIG. 1A), circular shapes (e.g., as illustrated in FIG. 6I), or the like. The islands also can be adapted to bind only selected cell types depending on the number and type of cell desired to be bound to particular islands. The islands may be between 1 and 2,500 square microns, between 1 and 500 square microns, between 1 and 500 square microns, between 1 and 300 square microns, or between 1 and 100 square microns in certain specific embodiments. In some applications, the islands can have an area of as little as between 1 and 50, or 1 and 20 square microns. Also, according to the invention, the islands may have any suitable lateral (i.e., shortest) dimension, for example, less than 100 microns, less than 50 microns, less than 20 microns or between 0.2 and 10 microns.

In one set of embodiments, the invention provides systems and methods for determining and analyzing cell migration and/or cell spreading behavior. Such cell motility assays can employ a variety of analytical techniques known in the art to quantify motility, including, for example, visible light, fluorescence, or electron microscopy, depending on the specific application. For example, as shown in FIGS. 1A-1D, cells capable of migration may be bound to cytophilic islands on a substrate separated by cytophobic SAMs; the substrate can then be exposed to an electric field which detaches the cytophobic SAMs (as previously described), thereby creating newly formed cytophilic region(s) on the substrate. Migration into the newly-created cytophilic regions may then be assessed using any of a variety of well-known suitable techniques, for example, through quantitative time-lapse microscopy as shown in FIGS. 1A-1D.

In one set of embodiments, a method of using certain articles and substrates of the invention for assaying the effects of various treatments and compounds such as drugs on cells is provided. In one embodiment, the invention provides the capability to assay the effects of various treatments or compounds on various cells adhered to a substrate. As one example, once a suspension of cells has been applied to a substrate containing cytophilic regions and SAM-coated cytophobic regions, a period of time is allowed to elapse in order to allow the cells to bind to the cytophilic regions of the substrate. Excess fluid including unbound cells may then be washed away. The cells may then be subjected to a treatment or exposed to a compound in situ or, in some situations, the cells may be pre-treated before being introduced to the substrate for attachment. The effects of the treatment or compound on the cells may then be individually assayed in a manner appropriate to the cell type and the treatment or compound being studied, for example, using analytical techniques such as those previously described.

In one set of embodiments, a cell motility assay of the invention can be automated. For example, in one embodiment, exposure of the substrate to the electric field, and/or detection of cell positions and/or migration behavior on the substrate may be automated, for example, with a computer or a mechanical system.

In some cases, a detector unit able to detect cell positions and/or cell migration behavior may include a multiplicity of individual detectors in an array corresponding and addressable to individual positions, regions, and/or islands on the substrate, as described above. For example, the detector may be a CCD camera or a semiconductor chip. In certain cases, the effect of a treatment or compound on many cells and/or cell types may be assessed simultaneously, with minimal user involvement.

In certain cases, the above-described embodiments, which allow for plating of cells at high densities, can be employed for high throughput tests of potentially useful treatments including pharmacological or toxicological compounds. In particular, the present invention provides assays which allow qualitative and quantitative changes in cell behavior or position in response to a change in the area over which they are permitted to adhere, to be determined and/or measured as a function of exposure to a given treatment or compound. In other embodiments, the inventive techniques can be utilized to assay various aspects related to the proliferation, differentiation, orientation, spreading, motility and/or migration of cells.

An enormous variety of patterns may be produced and a multiplicity of SAMs may be employed to create patterns of one or more types of cells. As discussed previously, the SAMs employed for embodiments involving cell binding and manipulation may be either generally or specifically biophilic/cytophilic or biophobic/cytophobic as applied (or certain surfaces may contain certain regions with generally biophilic/cytophilic or biophobic/cytophobic SAMs, while other regions contain specifically biophilic/cytophilic or biophobic/cytophobic SAMs). In some cases, the SAMs may be modified after SAM formation to become generally or specifically biophilic/cytophilic or biophobic/cytophobic by chemical modification of exposed functional groups. For example, when several SAMs are present in a pattern but only one is cytophilic, a first type of cell may be adhered to the cytophilic SAM and then a cytophobic SAM may be chemically modified in situ so as to become cytophilic. In some cases, a second cell type may then be adhered to the newly cytophilic SAM and this process can be repeated to create a complex pattern of different cell types. Similarly, if several SAMs are present in a pattern but only one is biophilic, a first type of biological entity may be adhered to the biophilic SAM and then a biophobic SAM may be chemically modified in situ so as to become biophilic. A second biological entity, may then be adhered to the newly biophilic SAM in some cases, and this process can be repeated to create a complex pattern.

In another aspect of the present invention, SAM-patterned substrates are provided which may be used to bind or adsorb proteins and/or other biological entities in specific and predetermined patterns. As is known to those of ordinary skill in the art, phenomena associated with the adsorption of proteins to solid synthetic materials are important in many areas of biotechnology including, for example, production, storage and delivery of pharmaceutical proteins, purification of proteins by chromatography, design of biosensors and prosthetic devices, and production of supports for attached tissue culture (see, for example, *ACS Symposium Series* 343, T. A. Horbett and J. L. Brash, Eds., Am. Chem. Soc., Wash., D.C., 1987; J. D. Andrade, Surface and Interfacial Aspects of Biomedical Polymers: Protein Adsorption, Plenum Press, N.Y., 1985; *Materials Research Society Proceedings* 252, L. G. Cima and E. Ron, Eds., Mat. Res. Soc., Pittsburgh, Pa., 1992). A number of researchers have demonstrated the formation of patterns of proteins (see, for example, A. S. Lea, et al., *Langmuir* 8:68-73, 1992). These have often relied on photolithography to create the patterns (see, for example, S. K. Bhatia, et al., *J. Am. Chem. Soc.*, 114:4432-4433, 1992; S. K. Bhatia, et al., *Anal. Biochem.*, 208:197-205, 1993). The present invention provides for relatively inexpensive and efficient patterning of proteins and manipulation of the affinity of a substrate for proteins via utilization of a non-chemical force-creating field and/or forces such as an electric field, with features of the pattern as small as 0.1-1 microns in some cases.

In similar embodiments, a substrate can be created with patterned SAMs thereon as described previously. Depending upon the desired application, the pattern may include islands or parallel rows of SAMs with different properties. One portion of the substrate may be biophilic/cytophilic and the other may be biophobic/cytophobic as applied, or they may be modified so as to become biophilic/cytophilic or biophobic/cytophobic subsequent to SAM formation, i.e., through exposure to an electric field as described. In a particular embodiment, a substrate surface may include a biophilic region of SAMs and a biophobic region of SAMs and, subsequent to binding a protein or proteins to the biophilic SAM, the biophobic region may be modified so as to become biophilic, i.e., through biophilic SAM removal via exposure to an electric field. In this way, a pattern of two or more protein groups may be created. Similarly, patterns of more than two SAMs may be used to create more complicated patterns of proteins in accordance with the present invention. The extent of binding of the proteins to the substrate may also be controlled and/or changed by the use of an electric field (or other non-chemical force-creating field). For example, proteins attached to SAMs present in certain portions of the substrate may be selectively detached by application of an electric field to those portions, in some cases without creating an electric field capable of SAM detachment in other portions of the substrate. In many embodiments, the electric field may be applied to the substrate to detach SAM-forming molecules as provided according to the invention even in the presence of animal serum (e.g., calf serum or human serum), or in the presence of other, undefined media (i.e., media in which the exact chemical composition is not known), whereas typical prior art techniques for electric field-mediated alteration of SAMs on surfaces do not have this capacity (see, e.g., Yousaf, et al., *Angew. Chem. Int. Ed.*, 40:1093, 2001).

In certain embodiments, a substrate with patterned proteins may be prepared as described above and cells may then be allowed to adhere to the patterned proteins to form a substrate having patterned cells thereon. In some embodiments, the proteins may include extracellular matrix proteins or ligands for receptors such as collagen, fibronectin or laminin; or specific cell receptors such as integrins. In certain embodiments, the patterned protein can mediate the cell adhesion behavior of the patterned cells. In yet another embodiment, a patterned substrate of biophilic and biophobic SAMs may be created and a wide variety of non-protein compounds may first be adhered to the pattern to mediate cell binding. Such compounds include but are not limited to sialic acid, lectins, polygalactose and other carbohydrates.

It should be understood that while the above examples are specifically directed to protein binding on the substrate, in other similar embodiments, any of a variety of other biomolecules could be utilized in place of or in addition to proteins, such as nucleic acids, saccharides, polysaccharides, lipids, fatty acids, hormones, vitamins, etc. In yet other embodiments, an inorganic or an organic synthetic or naturally occurring non-biomolecule (e.g., a synthetic drug candidate) may comprise an entity adhering to one or more regions of the substrate surface).

As is apparent from the description, the use of self-assembled monolayers that expose a variety of chemical functionalities on surfaces according to the invention is a common feature of many embodiments of the invention. In addition to the extensive and enabling description of various functional groups useful or potentially useful as exposed functionalities on SAMs utilized for particular purposes, additional disclosure related to hydrophobic, hydrophilic, biophobic, biophilic, cytophobic, cytophilic, and other functionalities incorporated into SAMs and/or SAM-forming molecules can be found in the following references, all incorporated herein by reference: U.S. Provisional Patent Application Ser. No. 60/443,446, filed Jan. 29, 2003, entitled "Alteration of Surface Affinities," by Jiang, et al.; U.S. Pat. No. 6,472,148, entitled "Molecular Recognition at Surfaces Derivatized with Self-Assembled Monolayers," by Bamdad, et al.; U.S. Pat. No. 6,368,838, entitled "Adhering Cells to Cytophilic Islands Separated by Cytophobic Regions to Form Patterns and Manipulate Cells," by Singhvi et al.; U.S. Pat. No. 6,355,198, entitled "Method of Forming Articles Including Waveguides via Capillary Micromolding and Microtransfer Molding," by Kim et al.; U.S. Pat. No. 6,180,239, entitled "Microcontact Printing on Surfaces and Derivative Articles," by Whitesides, et al.; U.S. Pat. No. 5,976,826, entitled "Device Containing Cytophilic Islands that Adhere Cells Separated by Cytophobic Regions," by Singhvi, et al.; U.S. Pat. No. 5,900,160, entitled "Methods of Etching Articles via Microcontact Printing," by Whitesides, et al.; U.S. Pat. No. 5,776,748, entitled "Methods of Formation of Microstamped Patterns on Plate for Adhesion of Cells and Other Biological Materials, Devices and Uses Therefor," by Singhvi, et al.; U.S. Pat. No. 5,512,131, entitled "Formation of Microstamped Patterns on Surfaces and Derivative Articles," by Kumar, et al.; U.S. Pat. No. 5,079,600, entitled "High Resolution Patterning on Solid Substrates," by Schnur, et al.; U.S. patent application Ser. No. 09/808,745, entitled "Cell Patterning Technique," by Ostuni, et al.; International Pat. Apl. Pub. No. WO 02/06407, entitled "Surfaces that Resist the Adsorption of Biological Species," by Whitesides, et al.; International Pat. Apl. Pub. No. WO 01/89788, entitled "Patterning of Surfaces Utilizing Microphilitic Stamps including Three-Dimensionally Arrayed Channel Networks," by Whitesides, et al.; Kleinfeld, et al., "Controlled outgrowth of dissociated neurons on patterned substrates," *Journal of Neuroscience*, 8(11):4098, 1988; Westermark, B., "Growth Control in Miniclones of Human Glial Cells", *Experimental Cell Research*, 111:295-299, 1978; Britland, S., et al., "Micropatterned Substratum Adhesiveness: a Model for Morphogenetic Cues Controlling Cell Behavior," *Experimental Cell Research*, 198:124-129, 1992; Singhvi, R., et al., "Engineering Cell Shape and Function," *Science*, 264:696, 1994; and Lopez, G. P., et al., "Convenient Methods of Patterning the Adhesion of Mammalian Cells to Surfaces Using Self-Assembled Monolayers of Alkanethiolates on Gold," *Journal of the American Chemical Society*, 115:5877-5878, 1993.

The following examples are intended to illustrate certain aspects of certain embodiments of the present invention, but do not exemplify the full scope of the invention.

EXAMPLE 1

This example describes a procedure for electrically desorbing self-assembled monolayers from a surface to release cells patterned on the surface from the constraints of those patterns.

In this example, a microcontact printing technique, described in more detail below, was used to pattern SAMs on a gold surface. To create SAMs on a surface that could confine cells into specific regions on the surface, an alkanethiol, HS—$(CH_2)_{17}$—$CH_3$ ("$C_{18}$"), and an $EG_3$-terminated thiol, HS—$(CH_2)_{11}$—(O—$CH_2$—$CH_2)_3$—OH ("$C_{11}EG_3$") were used. $EG_3$-terminated SAMs on the surface are able to resist the adsorption of proteins as well as resist the attachment and spreading of cells. Application of a cathodic potentials of about −1.2 V (with respect to a stainless steel electrode) on a gold surface can cause the SAMs to desorb. Removal of the $EG_3$-terminated SAMs from the surface then allowed the surface to adsorb proteins, for example, cell adhesion proteins present in solution.

Once the SAMs were patterned, cells were then patterned onto the surface, and were confined to regions coated with $C_{18}$ SAMs but excluded from $C_{11}EG_3$ SAM regions. An electric potential was then applied to the surface desorb the $C_{18}$ $EG_3$-terminated SAMs. By using this procedure, cells were plated in patterns, then released from those patterns. For instance, after desorption of the $EG_3$-terminated SAMs, cells were found to attach to, and spread across, previously cytophobic areas, as illustrated in FIGS. 1A-1D.

Micropatterned substrates were fabricated using a technique that has previously been described, for example, in Mrksich, M.; Dike, L. E.; Tien, J.; Ingber, D. E.; Whitesides, G. M., *Exp. Cell Res.*, 235:305-313, 1997. The substrate used was a No. 1 cover glass (Fisher Scientific, Chicago, Ill.) onto which a 2 nm thick layer of titanium had been evaporated (as an adhesion layer), followed by a 10-30 nm thick layer of gold by standard metal layer desorption techniques. A polydimethylsiloxane stamp with patterns for forming a printed pattern configured for plating cells in islands containing 2-3 cells each embossed on its surface was then inked with 2 mM of an ethanol solution of $C_{18}$, and dried under a stream of nitrogen. The inked stamp was brought into contact with the clean gold surface for about 2 s, and then was peeled away. Stamped gold substrates were immersed in 2 mM $C_{11}EG_3$ (synthesized as previously described, for example, in Pale-Grosdemange, C.; Simon, E. S.; Prime, K. L.; Whitesides, G. M., *J. Am. Chem. Soc.*, 113:12-20, 1991, incorporated herein by reference) in ethanol for 3 to 12 hours.

The micropatterned substrates were washed with Dubecco's phosphate buffer saline ("PBS"). Bovine capillary endothelial ("BCE") cells or NIH 3T3 fibroblasts (ATCC, Manassas, Va.) were plated directly onto these substrates at densities ranging from about 5,000 to about 100,000 cells per substrate (each gold substrate had an area of ~500 mm²) in Dubecco's modified essential medium media ("DMEM") containing 10% heat-inactivated calf serum ("CS"), supplemented with penicillin/streptomycin ("PS") and basic fibroblast growth factor (for BCE cells) or DMEM with 10% CS, PS and glucose (for fibroblasts). Cells were allowed to attach and spread for 12-24 hours at 37° C. in a 10% $CO_2$ atmosphere. After this step, the cells on the substrate appeared as shown in FIG. 1A.

Time-lapse images were acquired on a Leica inverted microscope equipped with a commercially available on-stage incubation chamber that maintained the temperature at 37° C. and the $CO_2$ concentration at 10% at all times. To prevent the evaporation of water, the culture dish was covered with a thin layer of mineral oil (Sigma-Aldrich, St. Louis, Mo.). Phase-contrast images were acquired by a Hamamatsu video camera using METAMORPH® software (Universal Imaging Inc., Downingtown, Pa.). Fluorescent images were acquired through a charge-coupled device from Hamamatsu (ORCA-ER). Quantification of cell shapes for the analysis of the fractional coverage of the surface was performed with an image analysis routine in Metamorph. Briefly, the cells were outlined and the total areas that the cells occupied were calculated. The calculated area was then divided by the total area of the field of view in the micrograph to obtain the normalized fractional coverage by cells. The LIVE/DEAD® assay kit was obtained from Molecular Probes (Eugene, Oreg.).

Figure 1B:
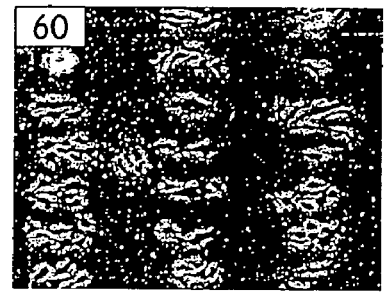
Figure 1C:
Figure 1D:
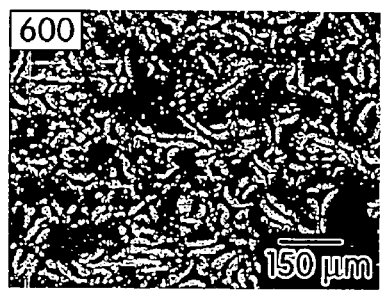
Figure 1E:
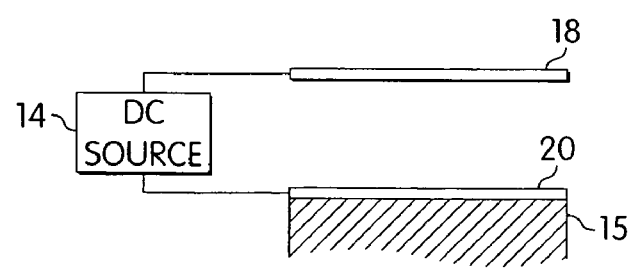
FIG. 1E is a schematic diagram of the apparatus used to apply voltage to the substrate shown in FIG. 1A, in accordance with one embodiment of the invention.

Referring to FIG. 1E, which illustrates the physical set-up for electric field application, to desorb the $C_{11}EG_3$ SAMs, a voltage pulse supplied by a constant DC power source 14 (BK Precision, Yorba Linda, Calif.) was applied between the substrate (cathode) 15 and a stainless steel electrode (anode) 18 in the medium for 30 seconds.

Electrical desorption of $EG_3$-terminated SAMs resulted in bovine capillary endothelial (BCE) cells confined to microislands of patterned SAMs being released from confinement, as illustrated in FIGS. 1A-1D. Patterning of BCE cells was accomplished by methods previously described, with $C_{18}$ as the protein-adsorbing SAM and $C_{11}$ $EG_3$ as the inert SAM. Cells were confined on these micropatterns in normal growth media for 24 hours. After application of a cathodic voltage pulse (−1.2 V vs. a stainless steel electrode for 30 seconds) (at time t=0 min in FIG. 1A), the cells began to spread measurably from the microislands (FIGS. 1B, 1C, and 1D for times of 60 min, 120 min, and 600 min, respectively, for the same field of view as FIG. 1A). The voltage pulse desorbed some or all of the $EG_3$-terminated SAMs, whereupon it is believed that extracellular matrix ("ECM") proteins such as fibronectin ("FN") present in the fluid medium or secreted by cells adsorbed onto regions that had been previously rendered inert by these SAMs. Thus, the cells were observed to migrate across the surface previously covered by the $C_{11}EG_3$ SAMs as if they were migrating on "bare" gold (i.e., gold with no SAM, but with a layer of proteins adsorbed from the medium). The cells were also observed to undergo normal growth and proceeded to cytokinesis on these newly cell attaching regions of the substrates.

The BCE cells appeared to be intact and normal after the voltage pulse utilized to detach the $C_{11}EG_3$ SAMs. The maximum voltage gradient tested was about −180 mV/mm (−1.8 V across a distance of 10 mm between the two electrodes) for a duration of 30 s in these experiments. Time lapse video microscopy showed that all cells had normal morphology and migrated normally on the surface after the voltage pulse. Preliminary analysis showed that the average speeds of migration of the cells were indistinguishable on the regions of the substrates subjected to electrical desorption of SAMs from those on a polystyrene petri dish. Additionally, a LIVE/

DEAD® assay showed that 99.9±0.05% of the cells had intact membranes and remained viable after a voltage pulse of about −1.8 V for about 30 s.

EXAMPLE 2

In this example, surface plasmon resonance ("SPR") experiments were performed on gold-coated substrates coated with $C_{18}$ and $C_{11}EG_3$ thiols. The SPR experiments were carried out as described previously, for example, in Sigal, G. B.; Mrksich, M.; Whitesides, G. M., *J. Am. Chem. Soc.*, 120:3464-3473, 1998. The gold-coated substrates were cut into 1 cm² pieces and incubated with the appropriate thiol. Various voltage pulses were applied to the gold-coated substrates in PBS before they were mounted onto the sensor chip for SPR analysis on a Biacore 1000 SPR Analyzer (Biacore Inc., Piscataway, N.J.).

Figure 2:
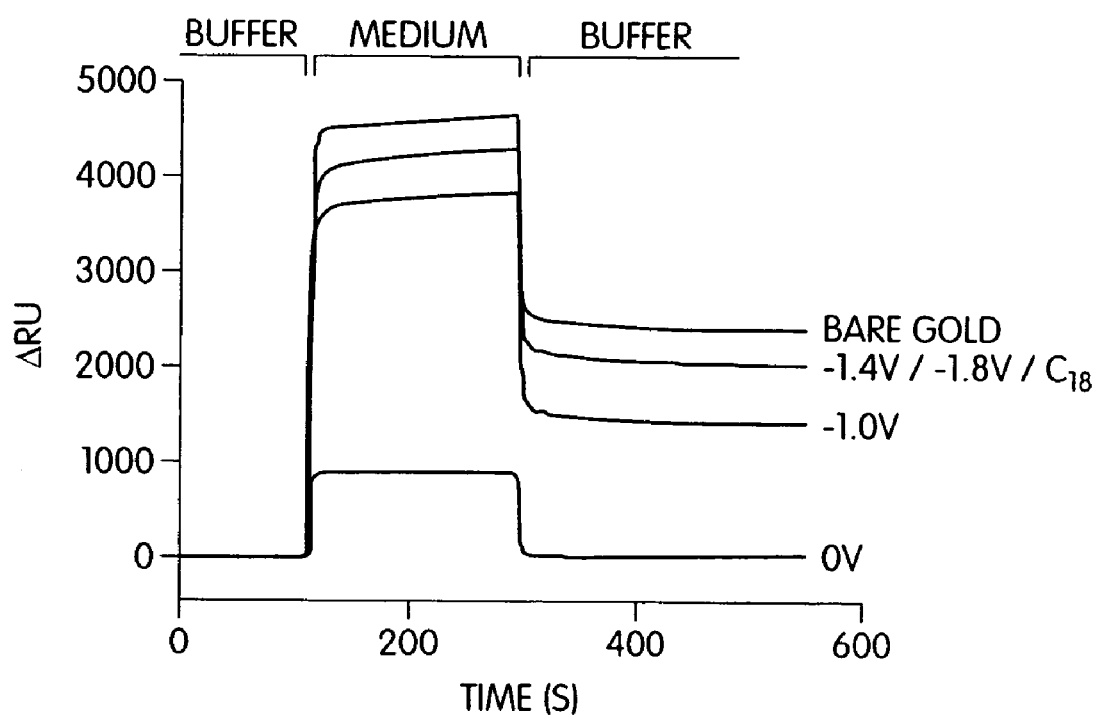
FIG. 2 is an SPR sensorgram illustrating various amounts of adsorbed proteins on a substrate after being subjected to different voltages, in accordance with an embodiment of the invention.

SPR sensorgrams as shown in FIG. 2 illustrate a comparison of the amounts of adsorbed serum proteins on the samples originally coated with $C_{11}EG_3$ after undergoing various cathodic voltages ranging from about −1.0 V to about −1.8 V for 30 s. The sensorgram on samples coated with a SAM formed by $C_{18}$ is also shown. The SPR data indicates an increase in the thickness of the thin organic film (SAMs and/or proteins) on the gold surface. This increase was reflected in the change in response units ("ΔRU"). ΔRU increases were mainly caused, it is believed, by the adsorption of proteins from the growth medium. The sensorgrams indicate that the gold surface ceased to be inert after a voltage pulse of about −1.0 V, and became similar to a $C_{18}$ SAM in its ability to adsorb proteins after pulses of about −1.4 V to about −1.8 V. Assuming that the ΔRU value for the sample having a SAM formed by $C_{18}$ thereon reflect that of a sample having adsorbed thereon as a complete monolayer of serum proteins, the coverage of proteins on the initially $C_{11}EG_3$ SAM-coated samples was estimated to be about 56% of a monolayer after the about −1.0 V pulse, and close to 100% of a monolayer after the about −1.4 V and about −1.8 V pulses. A bare gold surface was observed to adsorb slightly more proteins than a SAM of $C_{18}$.

Cyclic voltammetry was carried out in Dubecco's PBS solutions with a Pine Chem potentiostat (Pine Instrument Co., Grove City, Pa.). The SAM-coated gold surface 20 on substrate 15 was used as the working electrode while stainless steel electrode 18 was used as the counter electrode. No reference electrode was used. A scan rate of 100 mV/s was used.

Figure 4:
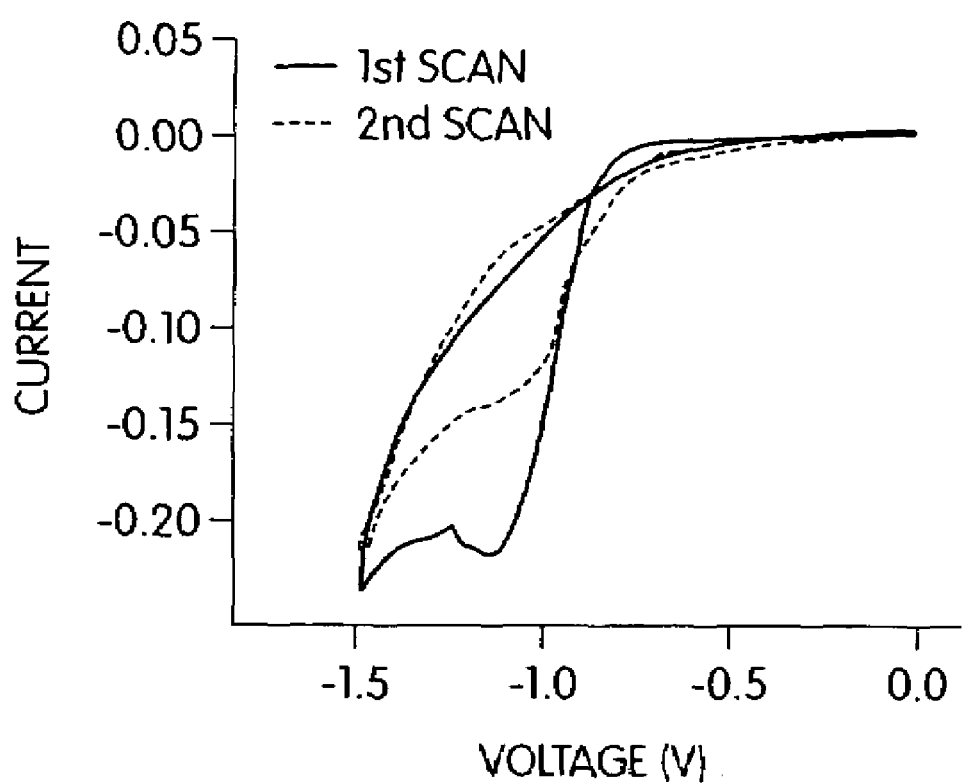
FIG. 4 is a graph that illustrates cyclic voltammogram data according to an embodiment of the invention.

Cyclic voltammetry data, for example, as illustrated in FIG. 4, also corroborated the description of $C_{11}EG_3$ from the substrate. The protein adsorptive capacity on the samples with SAMs formed by $C_{18}$ thiols thereon was not found to change substantially after application of voltage pulses in the ranges tested. Additionally, quantitative fluorescence measurements of rhodamine-labeled FN adsorbed on the $C_{18}$-covered area of the substrate (data not shown) was characterized by intensity values that were indistinguishable before and after the above-described voltage pulses, suggesting that those voltage pulses were able to selectively release $C_{11}EG_3$ SAMs but not $C_{18}$ SAMs from the substrate.

EXAMPLE 3

In this example, a method for screening agents whose biological activities are reflected in their influence on cellular motility is described.

BCE cells were patterned on a gold-coated substrate coated with $C_{18}$ and $C_{11}EG_3$ thiols in discrete patterned regions, similar to those shown in FIG. 1 by techniques similar to those described above in Example 1. Additionally, serum-containing media was used in some instances.

Figure 3:
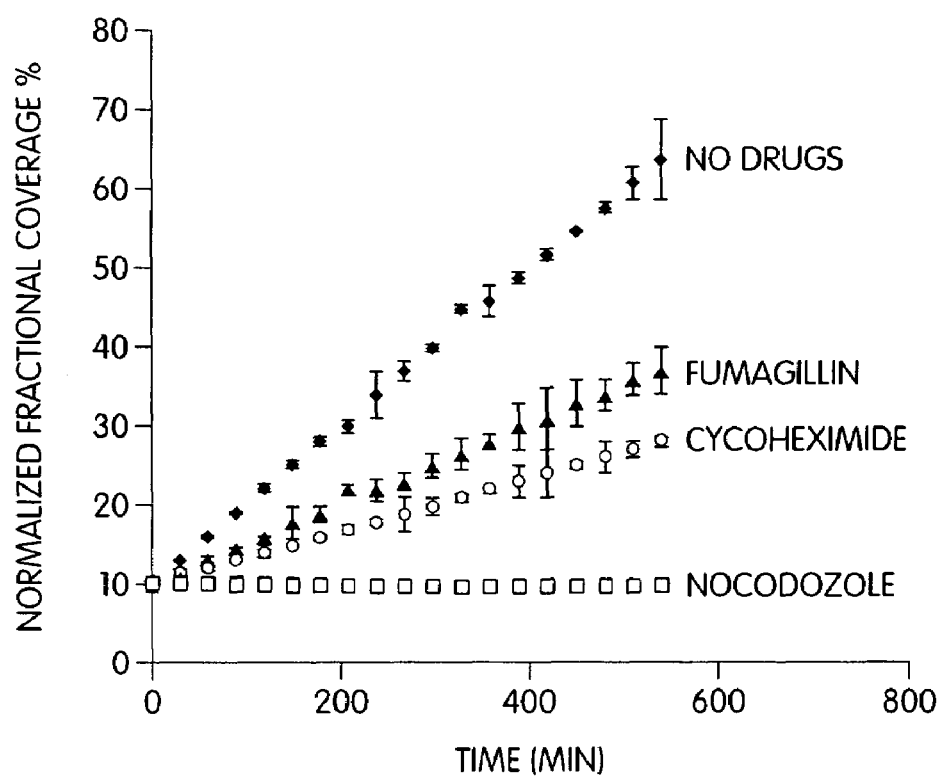
FIG. 3 is a graph that illustrates data from a cell-based screening assay in accordance with an embodiment of the invention, showing the effect of various drugs on cell motility.

When certain candidate drugs were added to the growth media before the voltage pulse, the migration of the cells out of the patterns was modified or completely abolished after the voltage pulse, as shown in FIG. 3 (data plotted as the normalized fractional coverage of the substrate (100%=fully confluent versus time). A summary of the influence of drugs on the motility of BCE cells after application of a voltage pulse (−1.2 V, 30 s) is shown in FIG. 3. Each datum in FIG. 3 represents the average of eight fields (i.e., islands as illustrated in FIG. 1A) of cells. Error bars represent one standard deviation from the mean. The calculation of fractional coverage is as described above in Example 1. The speed of cell movement out of the patterns provided a quantitative visual/optical screening for the effects of the screened drugs on the cells. Examples of drugs tested include fumagillin (100 mM), a drug that inhibits the motility of capillary cells, cycloheximide (1 mg/mL), a general inhibitor of protein synthesis, and nocodozole (1 mg/mL), a drug that depolymerizes microtubules.

Fumagillin and cycloheximide were observed to reduce the rates of cell migration, while nocodozole abolished it completely. The cells were also observed to resume normal migration after these drugs were removed (data not shown). Thus, this screening assay can be used to evaluate agents and/or treatments that are suspected to inhibit or promote cell motility, for example, for applications and/or treatment of conditions such as angiogenesis, inflammation, tissue morphogenesis, cancer, or wound healing.

Thus, this example illustrates one important application of the present invention; namely that of simplifying a class of inventive cell motility-based assays used in drug discovery. This example also illustrates that the inventive techniques can be used for fundamental studies of cell biology based on simultaneous spatial and/or temporal control of cell-substrate interactions.

EXAMPLE 4

This example illustrates a method for plating more than one cell type on a substrate, in accordance with one embodiment of the invention.

Figure 5A:
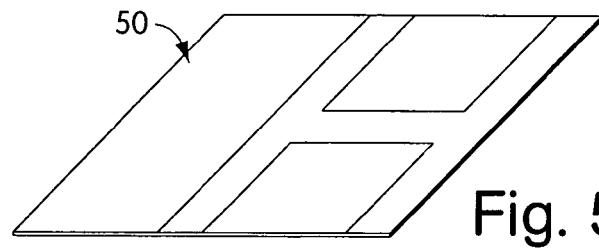
FIGS. 5A-5E are a series of schematic diagrams that illustrate a technique for patterning multiple cell types in accordance with one embodiment of the invention.
Figure 5B:
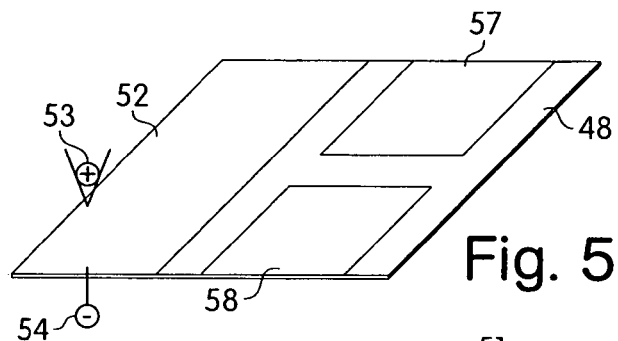

Reference is made to FIGS. 5A-5E, which schematically illustrate the materials used and method steps employed in this example. A glass substrate 50 was initially plated with gold, using conventional metal deposition techniques, to create discrete electrode regions 52, 57, 58 on substrate 50. Regions 52, 57, 58 were then plated with cytophobic $C_{11}EG_3$-terminated thiols to form SAMs covering each of those regions. The remaining non-electrode regions 48 were blocked with Pluronics® 127 (available from Wyandotte Chemicals Corporation, Wyandotte Mich.), as shown in FIG. 5B.

A reductive potential was applied to region 52 of the substrate using microelectrodes 53, 54, to "activate" region 52 for the attachment of cells, as shown in FIG. 1B. The reductive potential desorbed the thiols attached thereon from the substrate, thus allowing region 52 to become cytophilic or "activated." Cell type 55 was then plated onto region 52 using cell plating techniques known in the art, as shown schematically in FIG. 5C.

Figure 5C:
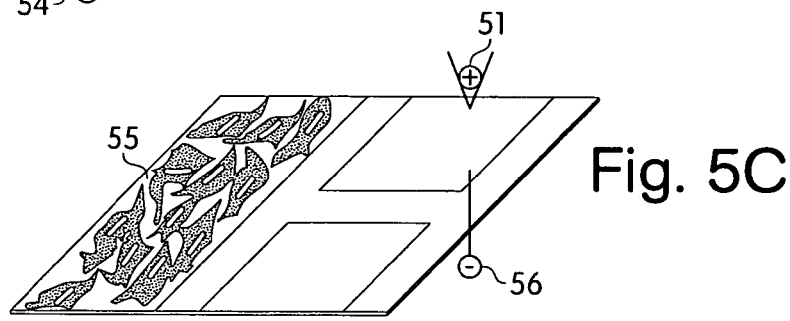
Figure 5D:
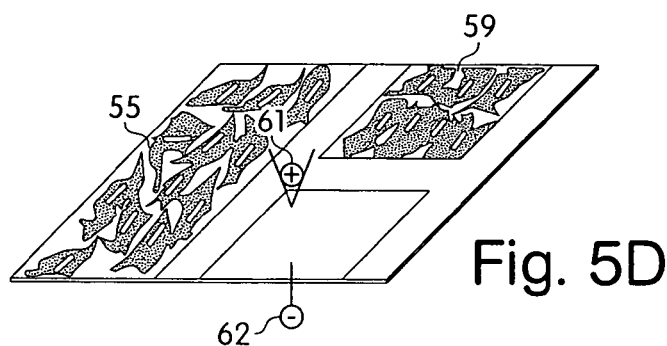
Figure 5E:
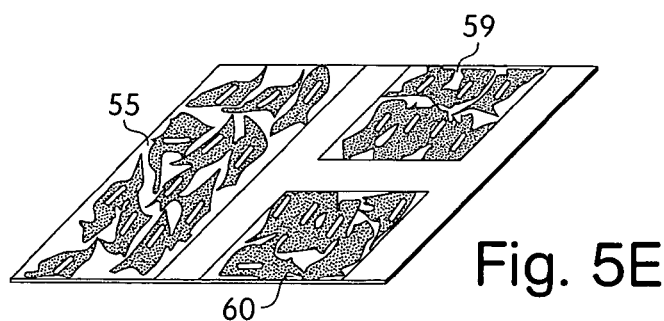

Similarly to FIGS. 5A-5C, a reductive potential was applied to region 57 using a pair of microelectrodes 51, 56 to activate region 57 by causing desorption of the cytophobic thiols attached thereon. After desorption of the SAM, a second cell type 59 was plated onto region 57 using cell plating techniques known in the art (FIG. 5D).

This process can be repeated as many times as desired. For example, in FIG. 5E, a reductive potential was applied to region 58 using a pair of microelectrodes 61, 62 to activate that region by causing desorption of the cytophobic thiols attached to that region. After desorption of the SAM, a third cell type 60 was plated onto region 59 using cell plating techniques known in the art.

EXAMPLE 5

This example illustrates that the ability to electrochemically release cells from a surface is compatible with SAMs formed from several alkanethiols and several types of motile mammalian cells.

Substrates to confine attachment of cells to particular geometries were generated as follows. A polydimethylsiloxane (PDMS) stamp molded from a master carrying defined microfeatures "inked" with $HS(CH_2)_{17}CH_3$ ("$C_{18}$") was brought into contact with a thin layer of Au (10–50 nm) deposited on a titanium-primed glass coverslip. This substrate was then incubated with an ethanolic solution of compounds (1), (2), (3) (see Table 1, below) or an aqueous solution of 1:1 mixture of (4) and (6), or (5) and (6), for 2-10 hours.

TABLE 1

| Number | Thiol Compound |
|--------|----------------|
| 1 | $HS(CH_2)_{11}(OCH_2CH_2)_{n=3-6}OH$ |
| 2 | $HS(CH_2)_3(OCH_2CH_2)_7OH$ |
| 3 | $HS(CH_2)_3(OCH_2CH_2)_{4-5}OH$ |
| 4 | $HS(CH_2)_{11}N(CH_3)_3^+Cl^-$ |
| 5 | $HS(CH_2)_{11}NH_3^+Cl^-$ |
| 6 | $HS(CH_2)_{11}S(O)_3^-Na^+$ |

The substrates were then coated with fibronectin (an extracellular matrix (ECM) protein), collagen, or an artificial polymer (polylysine) before plating one cell type onto these substrates in the appropriate cell culture solution. Typically, the cells formed patterns on these substrates within the first few hours of plating. Visual observations indicate that the cells could be confined to these patterns for at least four days. Table 2 lists the amount of time the patterns of cells remained faithful to the original pattern. After the indicated times, the cells grew out of the patterns of confinement and eventually formed a confluent monolayer on the substrate.

In another set of experiments using the same substrates as above, after allowing the cells to attach and spread to occupy the predetermined patterns (based on the pattern created using the stamp, above), a cathode of a direct current (DC) supply was connected to the gold-coated substrate, while the anode of the current supply was connected to the cell culture medium covering the cells (i.e., not the substrate). Voltages of between –0.6 V to 1.2 V were applied for about 30 seconds desorb the exposed SAM. The minimal voltage that allowed the cells to move out of their original patterns is listed in Table 1. Cell motility out of the original patterns was generally noticeable within the first hour after application of voltage.

Bovine capillary endothelial (BCE) cells (FIGS. 6A-6D), Normal Rat Kidney (NRK) cells (FIGS. 6E-6H), and COS-7 cells (6I-6L) were all released from confined patterns in these experiments (FIG. 6, the time in minutes after the application of voltage is indicated in the lower right of each image).

TABLE 2

| Compound Used | Time (Days) | Minimal Voltage for Release (V) |
|---------------|-------------|--------------------------------|
| 1 | 14-25 | 0.8 |
| 2 | 4-10 | 0.6 |
| 3 | 3-9 | 0.6 |
| 4 + 6 | 12-14 | 0.8 |
| 5 + 6 | 10-12 | 0.8 |

Thus, this example illustrates the release of motile mammalian cells from a surface using one embodiment of the invention.

EXAMPLE 6

This example illustrates the use of ellipsometry, surface plasmon resonance (SPR), and cell culture to characterize the ability of oligoethyleneglycol (OEG)-terminated self-assembled monolayers (SAMs) formed on palladium to resist adsorption of protein and adhesion of cells in vitro. An "inert" surface, as used in this example, is a surface that generally resists adsorption of significant amounts of proteins and adhesion of cells. Cells patterned on islands of methyl-terminated SAM surrounded by an OEG-terminated SAM on palladium remain confined to those islands for at least four weeks.

Four commercially-available thiols were used in these experiments: $HS(CH_2)_{11}(OCH_2CH_2)_3OH$ ("A"), $HS(CH_2)_{11}(OCH_2CH_2)_6OH$, ("B"); $HS(CH_2)_3(OCH_2CH_2)_7OH$, ("D"); and $HS(CH_2)_{17}CH_3$ ($C_{18}$) ("D"). Thiols A, B and C were known to form inert SAMs on gold. SAMs formed by $C_{18}$ on gold have been shown to promote the adsorption of proteins (see, e.g., Example 1). For the experiments using ellipsometry, 10-200 nm thick films of palladium were evaporated onto titanium- or chromium-primed substrates of glass or silicon wafers. Immersing the palladium films in 2 mM solutions of thiol for 2 to 55 hours then yielded the SAMs.

After incubating SAMs in fibroblast growth medium at 25° C. for 12 hours, ellipsometry was used to determine the quantity of adsorbed proteins on each type of SAM. The ability of inert surfaces to resist adsorption of all proteins from the growth medium can be a good indication of the inertness of the SAMs. The nominal thicknesses of the organic films adsorbed to each SAMs were calculated using an index of refraction of 1.45.

Figure 7:
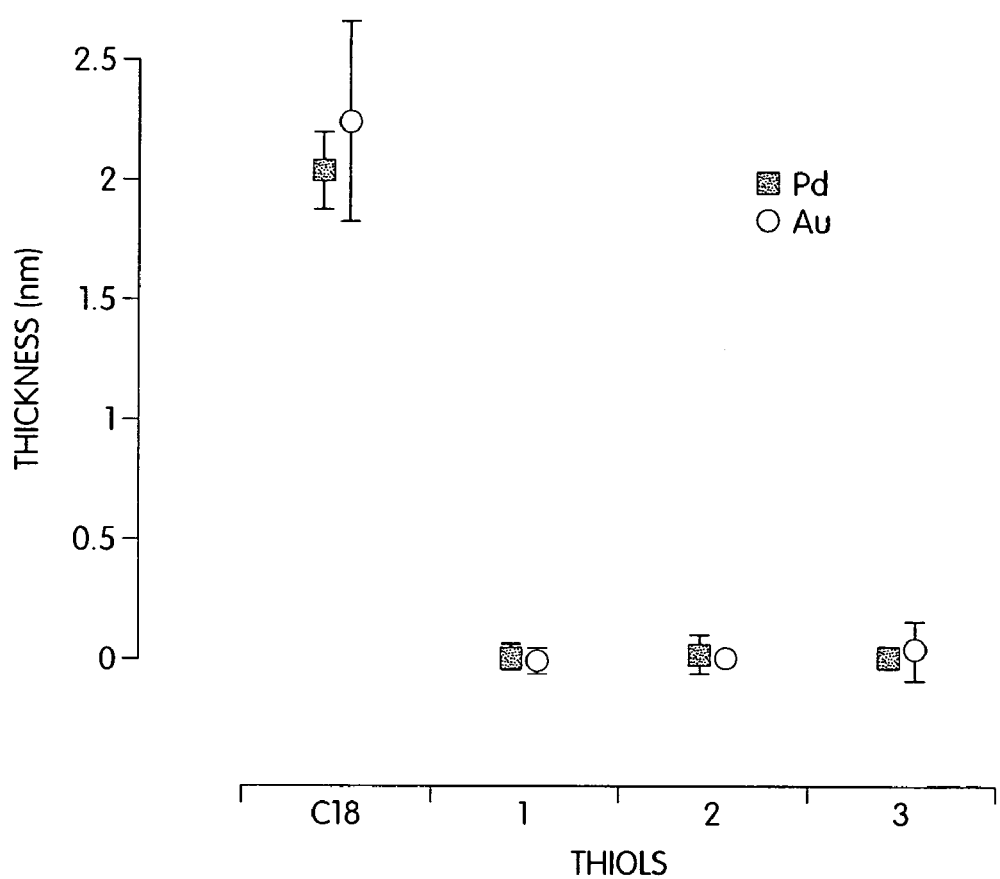
FIG. 7 is a graph of the nominal thickness of the film of protein adsorbed onto a SAM formed from various thiols on palladium and gold.

SAMs formed from thiols that terminate in OEG groups (i.e., SAMs A, B, and C) on palladium or on gold were found to have generally resisted the adsorption of proteins. The ellipsometry data showed no statistically significant increase in the thickness of the organic layer following incubation in medium. The SAM formed from $C_{18}$ on gold or palladium, however, were found to have strongly promoted the adsorption of proteins, as the ellipsometry data showed an increase in thickness of the dielectric layer on these SAMs by about 2 nm after incubation with fibroblast growth medium (see FIG. 7).

SAMs formed on a thin layer of Pd were used in some of these experiments. SAMs of $C_{18}$ on palladium were found to strongly promote adsorption of proteins, while SAMs of thiols A, B and C generally resisted the adsorption of proteins from the growth medium, as determined through SPR experiments (data not shown). Additional experiments illustrated that palladium and palladium-coated silver substrates were able to support the growth of cells for longer than 6 weeks (data not shown).

To test the ability of SAMs on palladium to support the adhesion and growth of cells in micropatterns, certain features on the substrates were defined using microcontact printing, using techniques similar to those described above. A poly(dimethylsiloxane) (PDMS) stamp that carried microfeatures was inked with 2 mM octadecanethiol ($C_{18}$) in ethanol, dried under a stream of nitrogen, then brought it into contact with the palladium films for 2 to 10 seconds. Next, the palladium film was immersed in ethanolic solutions containing 2 mM of thiols A, B, or C for up to 50 hours.

NIH 3T3 fibroblast cells were then cultured on these micropatterned substrates. The regions defined by the SAMs formed from $C_{18}$ supported the adhesion of cells, while the regions defined by thiols A, B, or C prevented the attachment of cells. On both gold and palladium, the 3T3 cells were found to have grown and divided only on regions covered by $C_{18}$ SAMs. A comparison of the cells after 2 days and after 2 weeks showed that the number of cells had increased dramatically and a full monolayer of cell has formed on each substrate within the regions defined by the SAMs. In contrast, OEG-terminated SAMs on the same substrate prevented the adhesion of cells during the same times.

It was found that some of the OEG-terminated SAMs resisted adsorption of protein and adhesion of cells for longer periods than other SAMs. On gold, SAMs formed by thiol B remained inert longer than the other SAMs on gold for about 2 weeks, but SAMs formed by thiol C on palladium rendered the surface inert for the longest period of time (4-6 weeks) of the thiols studied in this example.

Using features much smaller than a spread cell (5 micron dots separated by 5 microns), FIG. 8 shows that focal adhesions (FAs) may be localized. FAs are complexes of macromolecules that cells use to adhere to surfaces. FAs were identified via immunostaining for vinculin, a component of FAs. The area of substrate directly underneath attached cells appeared to undergo the most active remodeling by the cell.

Figure 8A:
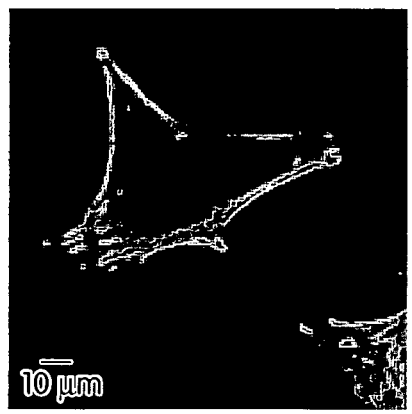
FIGS. 8A-8G are photocopies of a series of photographs of focal adhesion complexes in 3T3 cells.
Figure 8B:
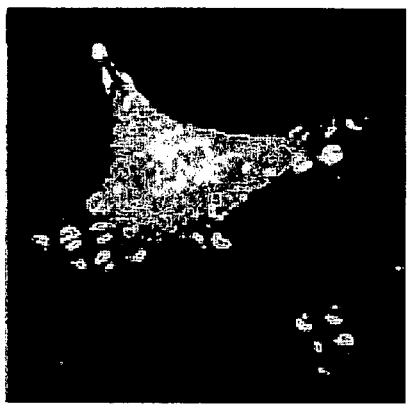
Figure 8C:
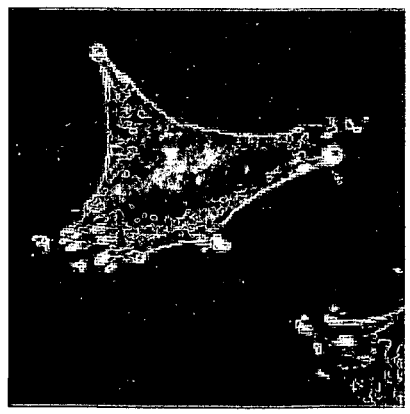
Figure 8D:
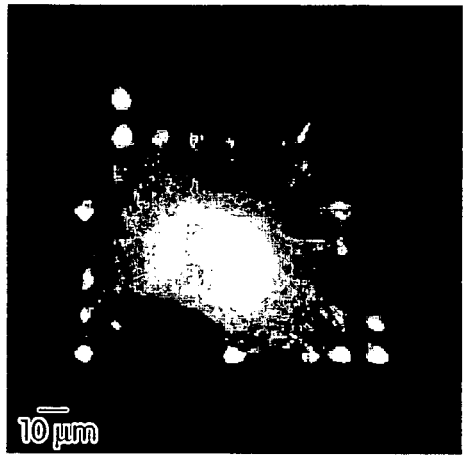
Figure 8E:
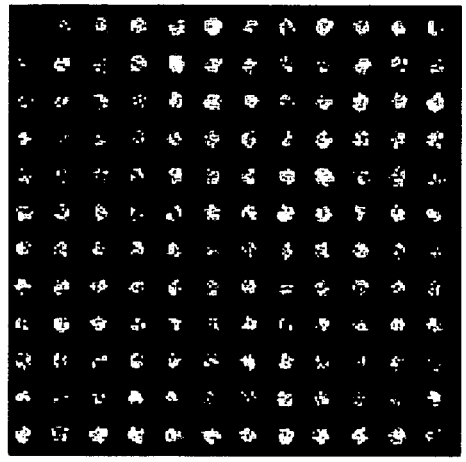
Figure 8F:
Figure 8G:
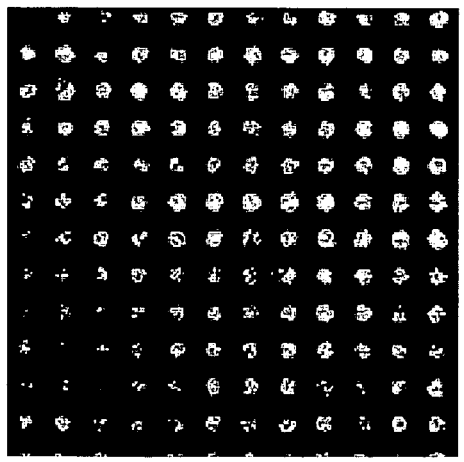

Thus, SAMs of OEG-terminated thiols on palladium can be used to investigate subcellular events on attached cells. In FIG. 8, FIG. 8A shows localization of actin, FIG. 8B shows localization of vinculin, and FIG. 8C shows the combination of FIGS. 8A and 8B. (FIGS. 8A-8C are all at the same magnification.) FIGS. 8D-8G illustrate a comparison of FAs on gold (FIGS. 8F and 8G) and palladium (FIGS. 8D and 8E). FIGS. 8D and 8F are cellular stains, while FIGS. 8E and 8G illustrate vinculin stains on the surface after the cells had been sheared off. (FIGS. 8D-8G are all at the same magnification.)

In conclusion, SAMs on palladium can be used to prepare inert surfaces for culturing patterned cells over long periods of time (>4 weeks). Confining patterned cells for long periods of time may be useful in studies of cellular behaviors that require long-term observation, for example, morphogenesis of tissues, oncogenesis, the effects of toxins on cells, etc. SAMs on palladium may also find uses in novel applications that carry out biological assays on devices fabricated using CMOS technologies.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

It should also be understood that, unless clearly indicated to the contrary, in any methods claimed herein that include more than one act, the order of the acts of the method is not necessarily limited to the order in which the acts of the method are recited.

The indefinite articles "a" and "an," as used herein in the specification and in the claims, unless clearly indicated to the contrary, should be understood to mean "at least one."

As used herein, "or" should be understood to mean inclusively or, i.e., the inclusion of at least one, but including more than one, of a number or list of elements. Only terms clearly indicated to the contrary, such as "only one of" or "exactly one of," will refer to the inclusion of exactly one element of a number or list of elements.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for determining mobility of cells comprising:
providing a surface having a first portion thereon and a second portion thereon, wherein the first portion is adjacent to the second portion of the surface, wherein the first portion of the surface is associated with a first electrode and the second portion of the surface is associated with a second electrode, wherein said first portion of the surface has molecules directly attached thereon at points of attachment of the molecules to the surface, wherein at least some of the molecules forming the self-assembled monolayer (SAM) on the first portion of the surface comprise a structure:

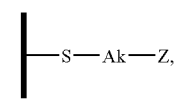

wherein ▌ comprises the first portion of the surface, Ak comprises an alkyl group, and Z comprises a terminal functional group that promotes attachment of cells, and wherein said second portion of the surface comprises self-assembled monolayer (SAM) forming molecules directly attached thereon at points of attachment, wherein the SAM attached to the second portion of the surface are unable to specifically bind cells;

exposing the surface having the first portion and the second portion to the cells, wherein the cells become attached to the first portion of the surface during the exposure;

altering the second portion of the surface by detaching at the point of attachment of the SAM forming molecules from the second portion of the surface by exposure of the second portion of the surface to an electric field so as to allow the second portion of the surface to then bind the cells; and determining mobility of the cells by monitoring migration of the cells from the first portion of the surface to the second portion of the surface.

2. The method of claim 1, wherein at least some of the molecules on the first portion of the surface comprise a hydrophilic domain.

3. The method of claim 1, wherein Z comprises a structure:

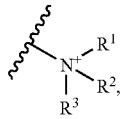

wherein $R^1$, $R^2$, and $R^3$ are each independently selected from the group consisting of H and an alkyl group.

4. The method of claim 1, wherein Z comprises a structure:

5. The method of claim 1, wherein the electric field has a magnitude that is at least about 100 V/m.

6. The method of claim 1, wherein the second portion of the surface is exposed to the electric field for at least about 5 s.

7. The method of claim 1, wherein the first portion of the surface comprises an array of molecules attached thereon.

8. The method of claim 1, further comprising exposing the second portion of the surface to a substance suspected of altering an interaction of the cell.

9. The method of claim 8, wherein the substance comprises a drug candidate.

* * * * *

UNITED STATES PATENT AND TRADEMARK OFFICE
CERTIFICATE OF CORRECTION

| | |
|---|---|
| PATENT NO. | : 7,659,053 B2 |
| APPLICATION NO. | : 11/181371 |
| DATED | : February 9, 2010 |
| INVENTOR(S) | : Xingyu Justin Jiang et al. |

It is certified that error appears in the above-identified patent and that said Letters Patent is hereby corrected as shown below:

In the Specification

Please replace the paragraph at Column 1, Line 14 with the following paragraph:
--This invention was made with government support under grant GM030367 awarded by the National Institutes of Health (NIH). The government has certain rights to this invention.--

Signed and Sealed this
Fifth Day of May, 2020

Andrei Iancu
*Director of the United States Patent and Trademark Office*